US012719039B1

(12) United States Patent
Fedick et al.

(10) Patent No.: US 12,719,039 B1
(45) Date of Patent: Aug. 25, 2026

(54) METHODS OF IDENTIFICATION AND CONFIRMATION OF SOLID MEDIA SAMPLES USING VIBRATIONAL SPECTROSCOPY COUPLED TO SPRAY IONIZATION MASS SPECTROMETRY SYSTEMS

(71) Applicants: The United States of America, as represented by the Secretary of the Navy, Arlington, VA (US); The Board of Trustees of Illinois State University, Normal, IL (US)

(72) Inventors: Patrick W. Fedick, Ridgecrest, CA (US); Christopher C. Mulligan, Bloomington, IL (US)

( * ) Notice: Subject to any disclaimer, the term of this patent is extended or adjusted under 35 U.S.C. 154(b) by 359 days.

(21) Appl. No.: 18/635,472

(22) Filed: Apr. 15, 2024

Related U.S. Application Data

(63) Continuation-in-part of application No. 18/121,375, filed on Mar. 14, 2023, now Pat. No. 12,409,451, which is a continuation-in-part of application No. 16/903,647, filed on Jun. 17, 2020, now Pat. No. 11,635,353.

(60) Provisional application No. 63/419,130, filed on Oct. 25, 2022.

(51) Int. Cl.

| | |
|---|---|
| ***H01J 49/02*** | (2006.01) |
| ***G01N 33/52*** | (2006.01) |
| ***H01J 49/00*** | (2006.01) |
| ***H01J 49/04*** | (2006.01) |
| ***H01J 49/44*** | (2006.01) |

(52) U.S. Cl.
CPC ............ *H01J 49/025* (2013.01); *G01N 33/52* (2013.01); *H01J 49/0036* (2013.01); *H01J 49/0086* (2013.01); *H01J 49/0459* (2013.01); *H01J 49/443* (2013.01)

(58) Field of Classification Search
CPC .......... H01J 49/00; H01J 49/02; H01J 49/025; H01J 49/0036; H01J 49/0086; H01J 49/0459; H01J 49/443; G01N 33/52
USPC ........................................ 250/281, 282, 288
See application file for complete search history.

(56) References Cited

U.S. PATENT DOCUMENTS

| | | | | |
|---|---|---|---|---|
| 4,879,458 A * | 11/1989 | Brunfeldt | H01J 49/0413 250/281 |
| 5,288,644 A * | 2/1994 | Beavis | H01J 49/0413 435/6.12 |
| 2002/0163642 A1* | 11/2002 | Zoval | B01L 3/5025 356/437 |
| 2003/0155500 A1* | 8/2003 | Syage | H01J 49/162 250/281 |
| 2004/0056187 A1* | 3/2004 | Krutchinsky | H01J 49/063 250/282 |

(Continued)

*Primary Examiner* — Jason L McCormack
(74) *Attorney, Agent, or Firm* — Naval Air Warfare Center; James M. Saunders

(57) ABSTRACT

The embodiments are directed to identifying and confirming the chemical composition of solid media samples. This includes collecting respective solid media samples and determining the solid media samples' vibrational spectra and mass spectra. The determination is made by using a system having a motorized platform, a computer, a vibrational spectrometer, a syringe pump, and a mass spectrometer. The vibrational spectra and mass spectra are then compared to each other to validate the chemical composition of the samples.

20 Claims, 15 Drawing Sheets

(56) References Cited

U.S. PATENT DOCUMENTS

2013/0334416 A1 * 12/2013 Satake ................ H01J 49/0431
250/288
2014/0104597 A1 * 4/2014 Sutin ...................... H01J 49/00
356/72

* cited by examiner 202
210
204
206
250

206
202
302
302
302
302
$a_2$
$b_2$
$b_1$
$c_1$
$a_1$
$c_2$

METHODS OF IDENTIFICATION AND CONFIRMATION OF SOLID MEDIA SAMPLES USING VIBRATIONAL SPECTROSCOPY COUPLED TO SPRAY IONIZATION MASS SPECTROMETRY SYSTEMS

CROSS-REFERENCE TO RELATED APPLICATIONS

This application is a continuation-in-part application claiming the benefit of U.S. nonprovisional application Ser. No. 18/121,375, filed on Mar. 14, 2023, the contents of which are hereby expressly incorporated by reference in its entirety and which priority is claimed. Nonprovisional application Ser. No. 18/121,375 claimed the benefit of U.S. provisional application No. 63/419,130, filed on Oct. 25, 2022. Nonprovisional application Ser. No. 18/121,375 also claimed the benefit as a continuation-in-part application claiming the benefit of U.S. nonprovisional application Ser. No. 16/903,647 filed on Jun. 17, 2020, the contents of which are hereby expressly incorporated by reference in its entirety and which priority is claimed, and which issued as U.S. Pat. No. 11,635,353 on Apr. 25, 2023.

STATEMENT REGARDING FEDERALLY SPONSORED RESEARCH OR DEVELOPMENT

The invention described herein may be manufactured and used by or for the United States of America for governmental purposes without the payment of any royalties thereon or therefor. The subject matter of this invention is related to work conducted under Navy contract NCRADA-NAWCWDCL-22-305.

FIELD

Embodiments generally relate to sampling and analysis platforms, systems, and methods.

Figure 1:
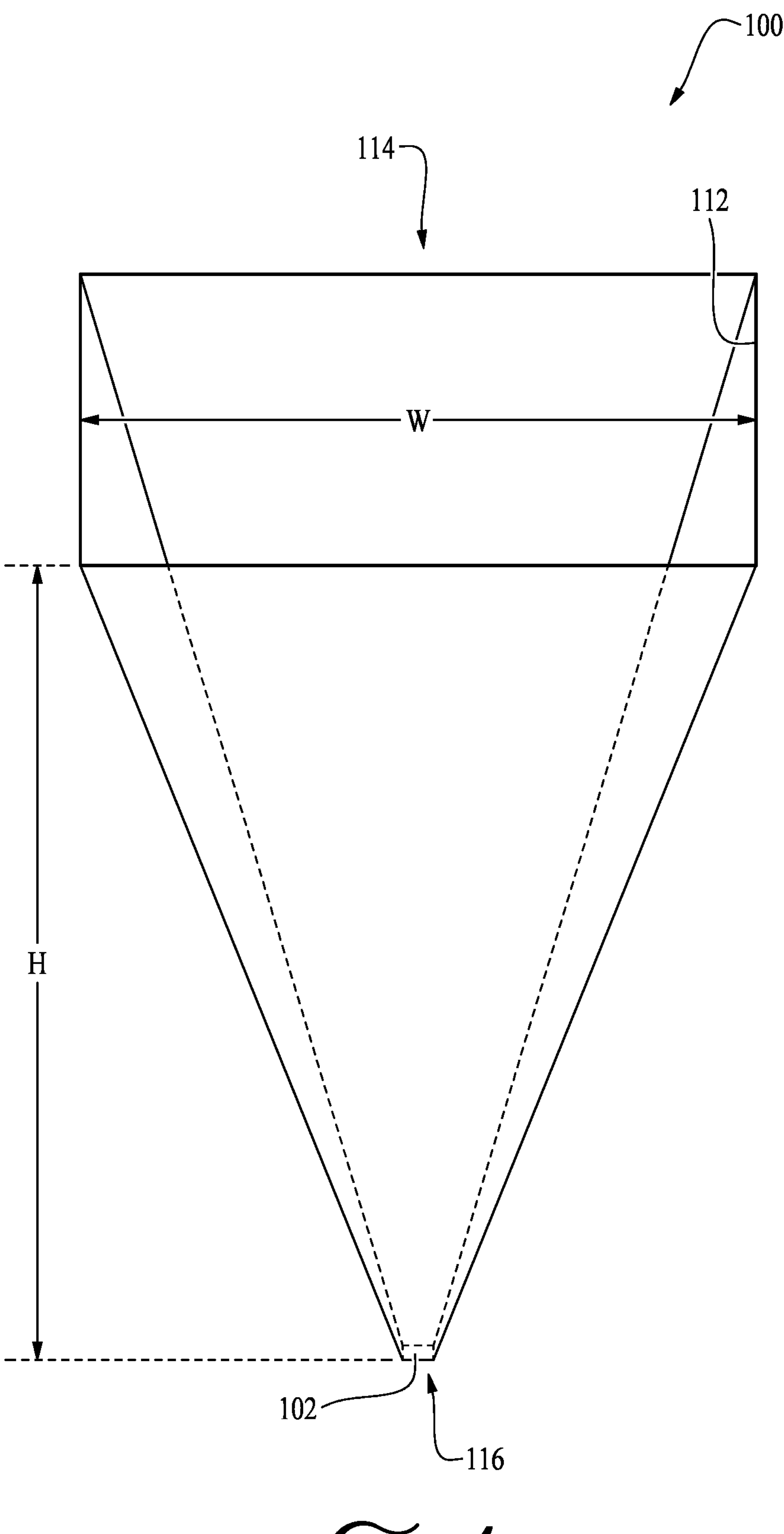
FIG. 1 illustrates an isometric view of a sample collection device, according to some embodiments.

It is to be understood that the foregoing general description and the following detailed description are exemplary and explanatory only and are not to be viewed as being restrictive, as claimed. Further advantages will be apparent after a review of the following detailed description of the disclosed embodiments, which are illustrated schematically in the accompanying drawings and in the appended claims.

DETAILED DESCRIPTION OF EMBODIMENTS

Embodiments may be understood more readily by reference in the following detailed description in connection with the accompanying figures. It is understood that embodiments are not limited to the specific devices, methods, conditions or parameters described and/or shown herein, and that the terminology used herein is for the purpose of describing particular embodiments by way of example only and is not intended to be limiting of the claimed embodiments.

The embodiments generally relate to sampling platforms and systems. In particular, the apparatus embodiments are configured to removably-hold sample collection devices. System embodiments include the apparatus in addition to components used in high throughput sample analysis. Some embodiments are sometimes referred to as a three-dimensional (3D)-printed cone spray ionization mass spectrometry (3D-PCSI-MS) sources. Other embodiments are simply referred to as apparatuses, systems, and methods. All embodiments have performed well in detecting and identifying analytes in bulk solids. In particular, working systems have shown increased throughput both in laboratory-based and in field conditions when components are coupled to systems employing a portable mass spectrometer (FIGS. 4 through 9) and systems and methods employing both a portable mass spectrometer and vibrational spectrometer, such as a Raman spectrometer and infrared (IR) spectrometer (FIGS. 10 through 13). Moreover, the systems and methods disclosed in FIGS. 10 through 13 are based on qualitative techniques, such as one may experience in the field. In particular, FIGS. 10 through 13, as disclosed herein, identify and confirm, i.e. validate the identification of a solid media sample's chemical composition and, if an analyte is present, determine the analyte's relative concentration.

Although the embodiments are described in considerable detail, including references to certain versions thereof, other versions are possible. Examples of other versions include varying component orientation or hosting embodiments on different platforms. Therefore, the spirit and scope of the appended claims should not be limited to the description of versions included herein.

Conventions, Parameters, and Terminology

At the outset, it is helpful to describe various conventions, parameters, and terminology associated with the embodiments.

Substantially

As used herein, unless otherwise specified, the term "substantially" refers to the complete, or nearly complete, extent or degree of an action, characteristic, property, state, structure, item, or result. As an arbitrary example, an object that is "substantially" surrounded would mean that the object is either completely surrounded or nearly completely surrounded. The exact allowable degree of deviation from absolute completeness may in some cases depend on the specific context. However, generally speaking, the nearness of completion will be so as to have the same overall result as if absolute and total completion were obtained.

The use of "substantially" is equally applicable when used in a negative connotation to refer to the complete or near complete lack of an action, characteristic, property, state, structure, item, or result. As another arbitrary example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

About

The use of "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. As such, it is understood that the ranges provided herein include the stated range and any value or sub-range within the stated range. For example, a range from about 0.15 millimeters to about 0.25 millimeters should be interpreted to include not only the explicitly recited limits from about 0.15 millimeters to about 0.25 millimeters, but also to include individual values, such as 0.18 millimeters, 0.20 millimeters, 0.21 millimeters, etc., and sub-ranges, such as from about 0.17 millimeters to about 0.20 millimeters. Additionally, one having ordinary skill in the art will recognize that the word "about" is often defined as "approximately," which is relied upon herein.

Removably Secure, Removably Hold, and Similar Variations

The embodiments make use of the terms "removably secure," removably-hold," "removably-secured," removably-held," and similar variations. The terms and similar variations are understood by one having ordinary skill in the art as being placed or mounted in such fashion that it is held in place, but which can be removed if so desired. Upon reading the description of the numerous embodiments, a person having ordinary skill in the art will understand the term in context, especially when viewing the associated figures.

High-Voltage

The term "high-voltage" herein is in the kilovolts (kV) range. In particular, the ranges from about four kV to about seven kV are included. Voltage levels both above and below this range are possible and are based on application-specific conditions, including anticipated sample constituents.

Sample

The embodiments are used to perform analysis using both vibrational and mass spectrometers. The term "sample" is sometimes used. In the embodiments, the sample is a solid media sample that may or may not contain an analyte. Effort is made to refer to the sample as a "solid media sample," however, at times, the terms "solid media" or simply "sample" may be used. At times, the terms "solid media containing an analyte," "solid media suspected of containing an analyte," or other similar variations may be used. In all instances, the "sample," i.e. the "solid media sample," is collected and placed in a sample collection device as discussed below. Although the interest is to identify the analyte and its relative concentration in the solid media sample, a person having ordinary skill in the art will recognize that the solid media sample may not contain analytes. Hence, the solid media sample may or may not contain an analyte and still be referred to as a "sample."

User, Analysist, and Operator

The terms "user," "analyst," and "operator" are used interchangeably herein. The terms may be used by themselves or in combination of two or all three of the terms. It is understood that all three terms are intended to be the person or person(s) using the embodiments described herein. It is also understood that these individuals are appropriately trained with using the various components discussed in the embodiments.

Tangible Medium

The term "tangible medium" is used in relation to displaying output from spectrometers such as the various peaks and troughs associated with both mass spectra and vibrational spectra. This includes displaying output on display monitors and display screens. Other tangible outputs are possible without detracting from the merits or generality of the embodiments. As such, in the embodiments, the tangible outputs may be shown and/or represented as a visual display screen depiction, hard copy printouts, as well as other media using the information such as, for example, a computer having computer-readable instructions that is configured to use output from the embodiments. Additionally, data obtained by the analysis can be shown and/or represented to a tangible medium for user verification, such as providing a visual verification to the user which could be useful before taking further action.

Apparatus, System, and Method Embodiments—FIGS. 2A Through 5 and FIGS. 10 Through 13)

In the accompanying drawings, like reference numbers indicate like elements. For all embodiments and figures, it is understood that the figures are not to scale and are depicted for ease of viewing. Reference characters 100, 200, 250, and 400 (FIGS. 2A through 5) depict various embodiments, sometimes referred to as mechanisms, apparatuses, devices, systems, and similar terminology. Reference characters 1000, 1200, 1205, and 1300 (FIGS. 10 through 13) build on these efforts with additional systems, apparatuses, and method embodiments. Several views are presented to depict some, though not all, of the possible orientations of the embodiments. It is understood a person having ordinary skill in the art knows how the various components discussed herein function, this includes, but is not limited to, procedures to collect solid media samples, placing sample container devices both containing solid media samples and those that do not contain solid media samples, into the various platforms discussed herein. One having ordinary skill in the art also understands how to use and connect the various components discussed, including how to assess analytical results produced. These components include computers, syringe pumps, mass spectrometers, and vibrational spectrometers. This also includes properly orienting the components for functional purposes and, when necessary, troubleshooting in the field.

Sampling Platform Apparatus and System—FIGS. 2A Through 5

Figure 2A:
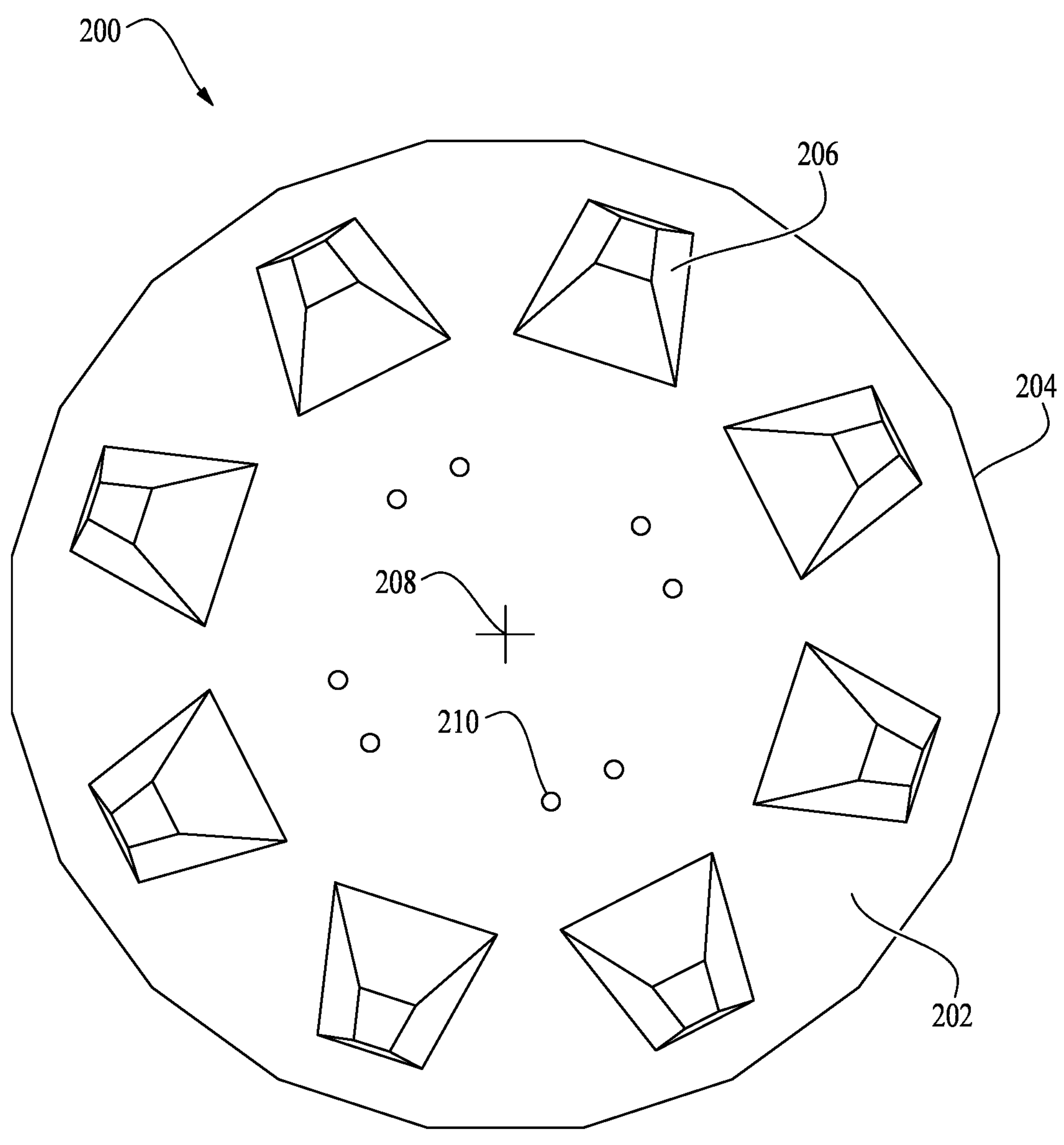
FIG. 2A illustrates a plan view of a sample collection apparatus having a plurality of receptacles, according to some embodiments.
Figure 2B:
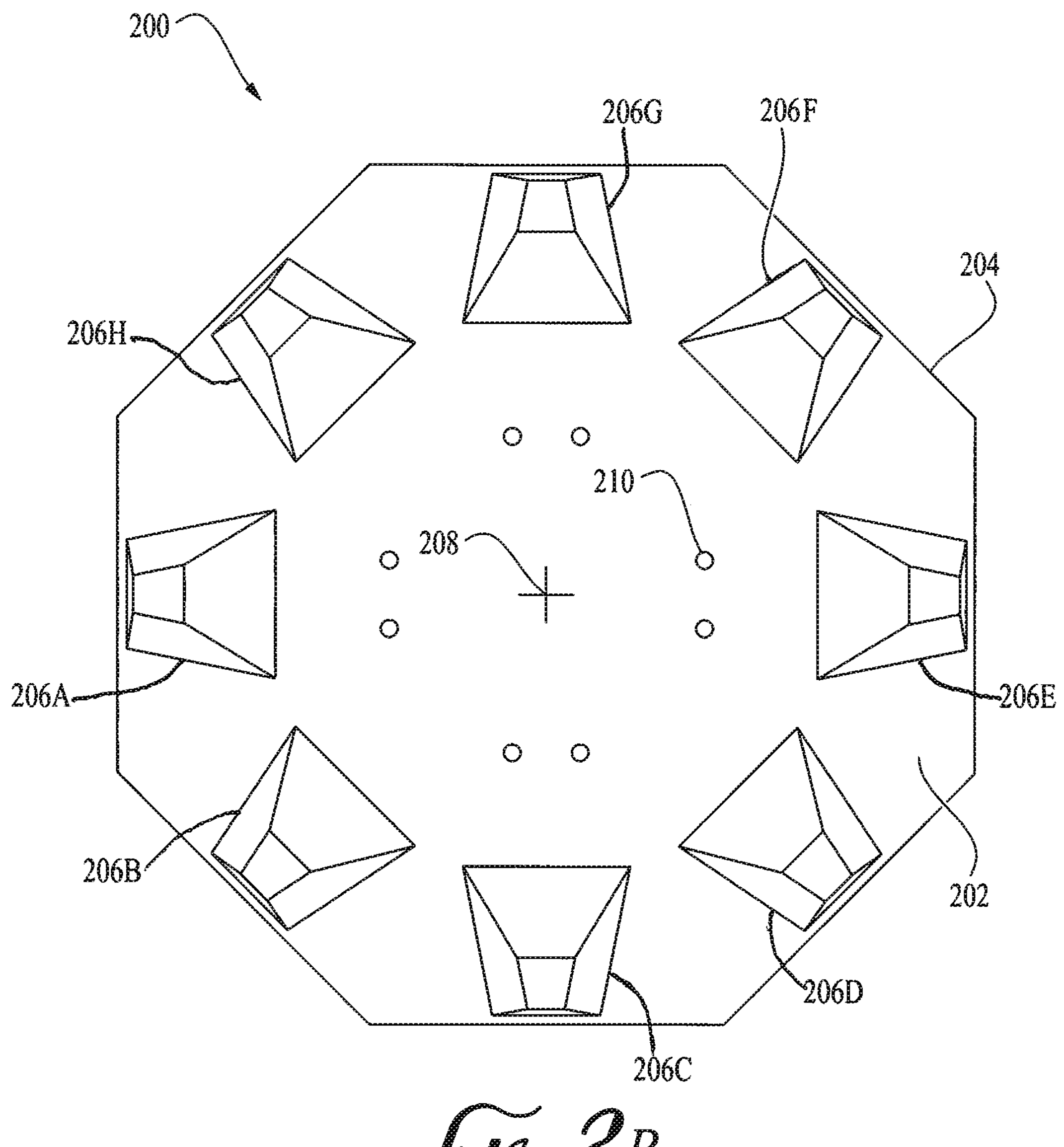
FIG. 2B illustrates a plan view of another sample collection apparatus having a plurality of receptacles, according to some embodiments.

FIG. 1 depicts an isometric view of a sample collection device 100. FIGS. 2A and 2B depict plan views of a sample collection apparatus 200. Although not exactly the same, the sample collection apparatuses 200 shown in FIGS. 2A and 2B are both disc-shaped and can be referred to as rotary.

Referring to FIG. 2A a sample collection apparatus 200 is shown. The sample collection apparatus 200 can also be referred to as a sampling platform, a sample collection device holder, an autosampler, an apparatus, a platform, and similar variations. Referring to FIGS. 2A and 9 simultaneously, the sample collection apparatus 200 is a platform having a first side 202, a second side 802 (FIG. 8), and an outer edge 204. The first and second sides 202 and 802 can also be referred to as top and bottom sides, or upper and lower sides, respectively. A plurality of receptacles 206 extend through the platform 200 from the first side 202 to the second side 802. As such, the receptacles 206 perforate through both the first and second sides 202 and 802 and each receptacle in the plurality of receptacles can be referred to as an aperture or similar terminology without detracting from the merits or generalities of the embodiments.

Figures 2C, 3:
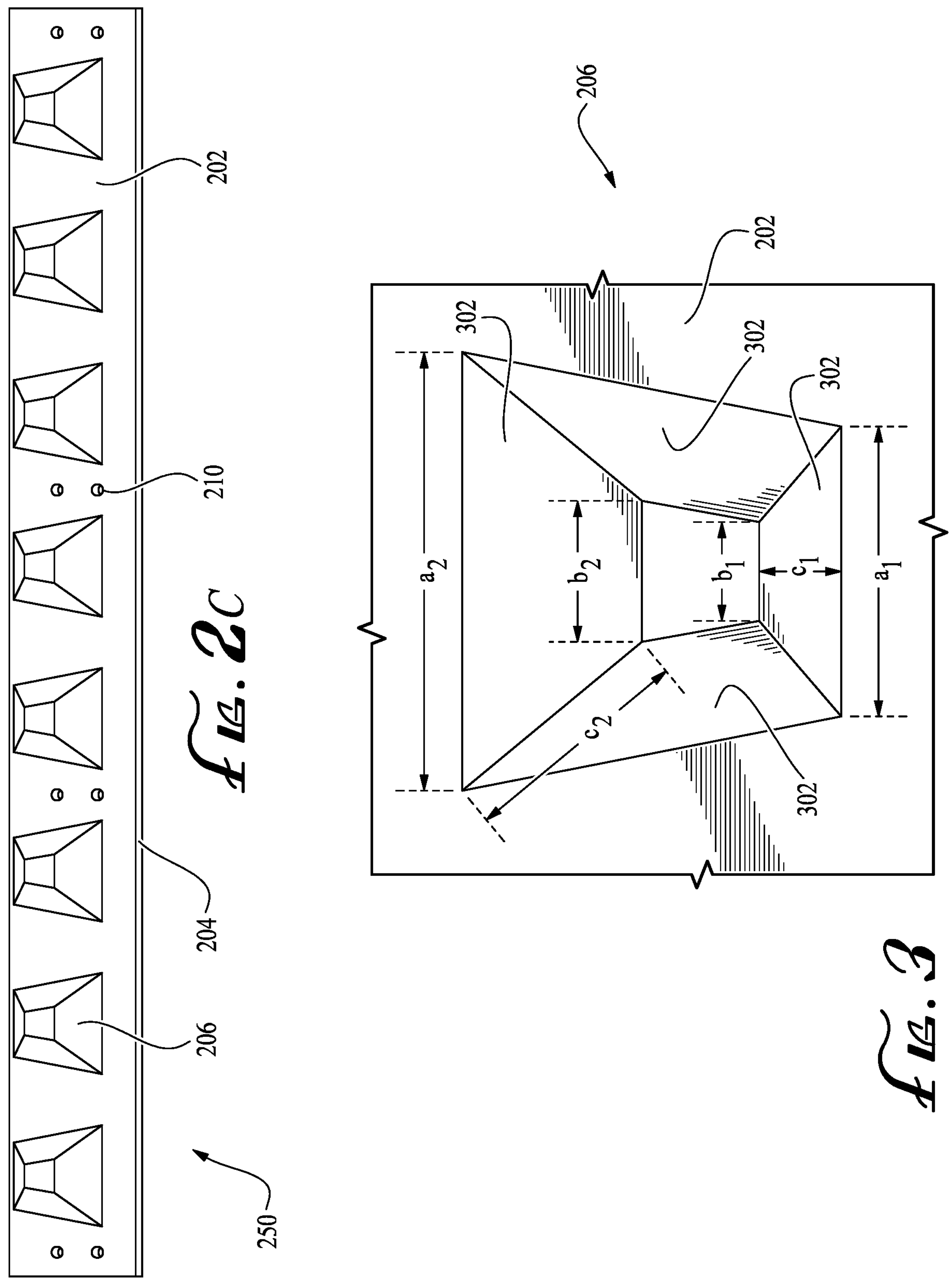
FIG. 2C illustrates a plan view of yet another sample collection apparatus having a plurality of receptacles, according to some embodiments.
FIG. 3 illustrates a close-up view showing the geometry of a single receptacle, according to some embodiments.

Each receptacle in the plurality of receptacles 206 is configured to removably-hold a sample collection device 100 (shown in FIG. 1). Similarly, it can be equally said that each receptacle in the plurality of receptacles 206 is configured to receive or cradle the sample collection device 100. In practice, the number of sample collection devices 100 would match the number of receptacles in the plurality of receptacles 206. FIG. 3 shows a close-up view of a single receptacle in the plurality of receptacles 206. Importantly, it is evident that each receptacle in the plurality of receptacles 206 has inner walls 302 cooperating with the geometry of the sample collection device 100. Although four inner walls 302 are shown, it is understood that fewer or greater than four inner walls can be used without detracting from the merits or generalities of the embodiments. Additionally, the inner walls 302 shaped for quick alignment of the sample collection device 100. It is understood that the sample collection devices 100 fit in the receptacles 206 and held in place through either lost motion due to the geometry of the inner walls 302 or by friction fit with the inner walls.

As the shapes and dimensions of the sample collection device 100 can vary, so too can the shapes and dimensions of the receptacles 206. The receptacle 206 shown in FIG. 3 is typical of the receptacles in some embodiments. However, it is understood that dimensions and shapes in all embodiments for all components can be varied based on application-specific conditions. The receptacle 206 shown in FIG. 3 resembles a trapezoidal shape at both the first and second surfaces 202 and 802 of the sample collection apparatus 200. At opposing sides of the receptacle 206 at the first side 202, at least one dimension is two centimeters (shown as a1 in FIG. 3) and at least one dimension is three centimeters (shown as a2 in FIG. 3), with the respective sides parallel to each other. Similarly, at opposing sides of the receptacle 206 at the second side 902, at least one dimension is 0.6 centimeters (shown as b1 in FIG. 3) and at least one dimension is one centimeter (shown as b2 in FIG. 3), with the respective sides parallel to each other.

The inner wall nearest the outer edge 204 is vertical, i.e. perpendicular to the first and second sides 202 and 802, and has a dimension of 1.4 centimeters (shown as c1 in FIG. 3). The inner wall nearest the central longitudinal axis 208, i.e. farthest from the outer edge 204 is slanted at about 37 degrees from the first side 202 to second side 802 to accommodate proper fit for the sample collection devices 100 in the receptacles 206 for sample analysis. The intersection of at least two interior walls 302 forms creates an intersection distance of 2.5 centimeters (shown as c2 in FIG. 3) from the first side 202 to the second side 802. It should be noted that the dimensions and geometry shown is not to be construed as limiting, but is only for illustrative purposes.

Referring to FIG. 1, the sample collection device 100 has a proximal end 114 and a distal end 116. The distal end 116, which can also be referred to as a tip, has a hole 102 with a diameter range of about 0.15 millimeters to about 0.25 millimeters. The sample collection device 100 also includes a hollow interior 112 that forms a cavity, which can hold a solid media sample. The sample collection device 100 can be any hollow shape that terminates at a point and that can hold a solid media sample while allowing solvent extraction from the device during ambient ionization for mass spectrometer analysis. This diameter of the hole 102 has proven to be small enough to retain a solid media sample, but is large enough to allow solvent to exit during mass spectrometric analysis. The hole 102 allows for analysis via ambient ionization after the solvent has passed through the solid media and solvent extraction of analyte has occurred.

The sample collection device 100 also has a height and a width, shown as h and w, respectively, in FIG. 1. The height h and width w can be any height and width that is large enough to hold a solid media sample, but small enough to remain portable while using the least amount of material as possible. The height h is defined as the vertical distance from the hole 102 at the distal end 116 of the sample collection device 100 to the proximal end 114. The width w is defined as the furthest distance from the inner side of a wall to the opposite inner side of a wall of the sample collection device 100. In an embodiment, the sample collection device 100 may have a height h and a width w ranging from about 12.5 millimeters to about 40 millimeters.

The sample collection device 100 also has a thickness that is large enough to hold a solid media sample, but small enough to retain the device's original shape while using the least amount of material as possible. The sample collection device's 100 thickness is defined as the distance from the inner side of a wall to the outer side of a wall. In an embodiment, the sample collection device 100 has a thickness ranging from about 0.6 millimeters to about 3 millimeters. The sample collection device 100 can be made using any known methods to produce a conductive polymer device, including 3D printing. Once produced, the sample collection device 100 can be used immediately to collect samples for mass spectrometer analysis.

The sample collection device 100 is made of a conductive polymer. The conductive polymer includes a mixture of carbon nanotubes and a polymer. Alternatives to the carbon nanotubes include metal-infused polymers such as, for example, copper and conductive resins. The polymer may be any polymer that can be subjected to a voltage and is immiscible with the extraction and spray solvent. For example, the polymer may be polyethylene terephthalate, acrylonitrile butadiene styrene, polylactic acid, polyetherketoneketone, polyether ether ketone, polycarbonate, polyphenylene sulfide, polyvinylidene fluoride, and combinations thereof. The carbon nanotubes may be any carbon nanotubes that conduct electricity. An example of the carbon nanotubes is multi-wall carbon nanotubes.

The platform 200 has a central longitudinal axis 208. The plurality of receptacles 206 are axially-spaced at equal distance about the central longitudinal axis 208. The platform 200 is, in several embodiments, generally a disc and is sometimes referred to as disc-shaped, rotary-shaped, or substantially-circular. The platform 200 can also be referred to as rotary, a rotary disc, or rotary platform. It is evident when viewing FIGS. 2A, 2B, and 4 through 8 that the sample collection apparatus 200 is polygonal in plan view, i.e. is a polygonal shape, while still maintaining a rotary or substantially-circular, disc shape. FIG. 2A depicts the outer edge 204 as having twenty sides. Whereas, FIGS. 2B and 4 through 8 show the platform 200 having its outer edge 204 defined by eight sides, i.e. being octagonal in plan view or having an octagonal shape. In all instances, it is evident that all of the above shapes are applicable without detracting from the merits or generalities of the embodiments. Likewise, the sample collection apparatus 200 is not specifically limited to the number of sides forming its outer edge 204.

The rotary, disc-shaped platforms in FIGS. 2A and 2B are about 16 centimeters in diameter. The distance between diametrically-opposed receptacles 206, i.e. receptacles 180 degrees apart is about 10 centimeters. The platform 200 thickness, measured parallel to the central longitudinal axis 208 and perpendicular to the first and second sides 202 and 802 is about 1.4 to about 1.5 centimeters, however it can range from about one centimeter to about ten centimeters, depending on application-specific conditions. It is understood that the dimensions can be varied to accommodate larger or smaller platforms 200, as well as different receptacle 206 geometries and dimensions.

FIG. 2C illustrates another embodiment, depicted with reference character 250, of the sample collection apparatus shown in a linear rail orientation. The sample collection apparatus 250 in FIG. 2C is a platform and is rectangular in shape and also has a plurality of receptacles 206 through both sides of the platform. As before, the first side is depicted with reference character 202. The second side is not viewable in FIG. 2C, but a person having ordinary skill in the art will recognize that the linear rail orientation platform 250 includes the second side. The outer edge 204 forms the rectangular shape of the sample collection apparatus 250 in FIG. 2C. As before, the receptacles 206 in the sample collection apparatus 250 in FIG. 2C are configured to accommodate sample collection devices 100, both in number and the previously discussed dimensions and geometries. The sample collection apparatus 250 in FIG. 2C has thickness is about 1.4 to about 1.5 centimeters, however it can range from about one centimeter to about ten centimeters, depending on application-specific conditions.

In some embodiments, the number of receptacles in the plurality of receptacles 206 is a range of about four to about twelve receptacles and, hence, the number of sample collection devices 100 would also be a range of about four to about twelve devices. In other embodiments, the range can be greater such as, for example, three to twenty receptacles 206 and sample collection devices 100. As such, any number of receptacles 206 and sample collection devices 100 can be used, based on the dimensions of the sample collection apparatuses 200 and 250, without detracting from the merits or generalities of the embodiments.

In the disc-shaped, rotary-shaped, or substantially-circular embodiments in FIGS. 2A, 2B, and 4 through 8, the axial spacing is a range of about 30 degrees to about 90 degrees. The plurality of receptacles 206 in the linear rail orientation (250 in FIG. 2C) are in a series arrangement with equal spacing between adjacent receptacles. The figures, for ease of viewing, depict the plurality of receptacles 206 has being eight receptacles, but it is understood that any number can be used based on application-specific conditions. For instance, in other disc-shaped, rotary-shaped, or substantially-circular embodiments, the axial spacing can be a range of about 18 degrees to about 120 degrees, based on the dimensions of the sample collection device 200.

The sample collection device 100 is hollow and is configured to hold a solid media sample containing an analyte. In some embodiments, the sample collection device 100 is a hollow multi-faced pyramid. In other embodiments, the sample collection device is a hollow cylindrical cone. The polymer of the sample collection device 100 is selected from the group consisting of polyethylene terephthalate, acrylonitrile butadiene styrene, polylactic acid, polyetherketoneketone, polyether ether ketone, polycarbonate, polyphenylene sulfide, polyvinylidene fluoride, and combinations thereof.

The solid media is selected from the group consisting of soil, sand, sediment, waste, pure analytes, and combinations thereof. Toxicology samples and analysis can be included in the embodiments, based on application-specific conditions. The analyte is selected from the group consisting of perfluoroalkyl substances, polyfluoroalkyl substances, energetics, chemical warfare agent simulants, drugs of abuse, pesticides, and combinations thereof. Any perfluoroalkyl substances, polyfluoroalkyl substances, energetics, chemical warfare agent simulant, drugs of abuse, or pesticides known to those skilled in the art may be used as the analyte depending on the purpose of evaluating the solid media. Some specific examples of perfluoroalkyl substances include perfluorodecanoic acid, heptafluorobutyric acid, perfluorotridecanoic acid, perfluoroheptanoic acid, perfluorooctane-sulfonic acid, perfluoroundecanoic acid, perfluorooctance-sulfonamide, tridecafluorooctane-1-sulphonic acid, perfluorooctanoic acid, perfluorononanoic acid, tricosafluorododecanoic acid, or combinations thereof.

The sample collection apparatuses discussed—both rotary or disc-shaped 200 and rectangular or linear rail 250 versions, are made from non-conductive, chemically-inert plastics. Suitable materials for the sample collection apparatuses 200 and 250 include plastics such as polylactic acid (PLA), polyethylene terephthalate glycol (PETG), and acrylonitrile butadiene styrene (ABS). Fabrication techniques of the sample collection apparatuses 200 and 250 include 3-D printing and machining techniques such as computerized numerical control (CNC) and injection molding.

Samples in the sample collection devices 100 are not shown in some figures for ease of viewing, especially due to the vast differences in substances that can be analyzed. Samples, i.e. solid media for analysis, can consist of the analyte in its solid form (powders, pressed powders, tablets, crystals, etc.) or an analyte within, or upon, a solid matrix (i.e. per—and polyfluoroalkyl substances (PFAS) in soil, sediment, or solid waste). The solid samples can be scooped or shoveled into the sample collection device 100.

Figure 4:
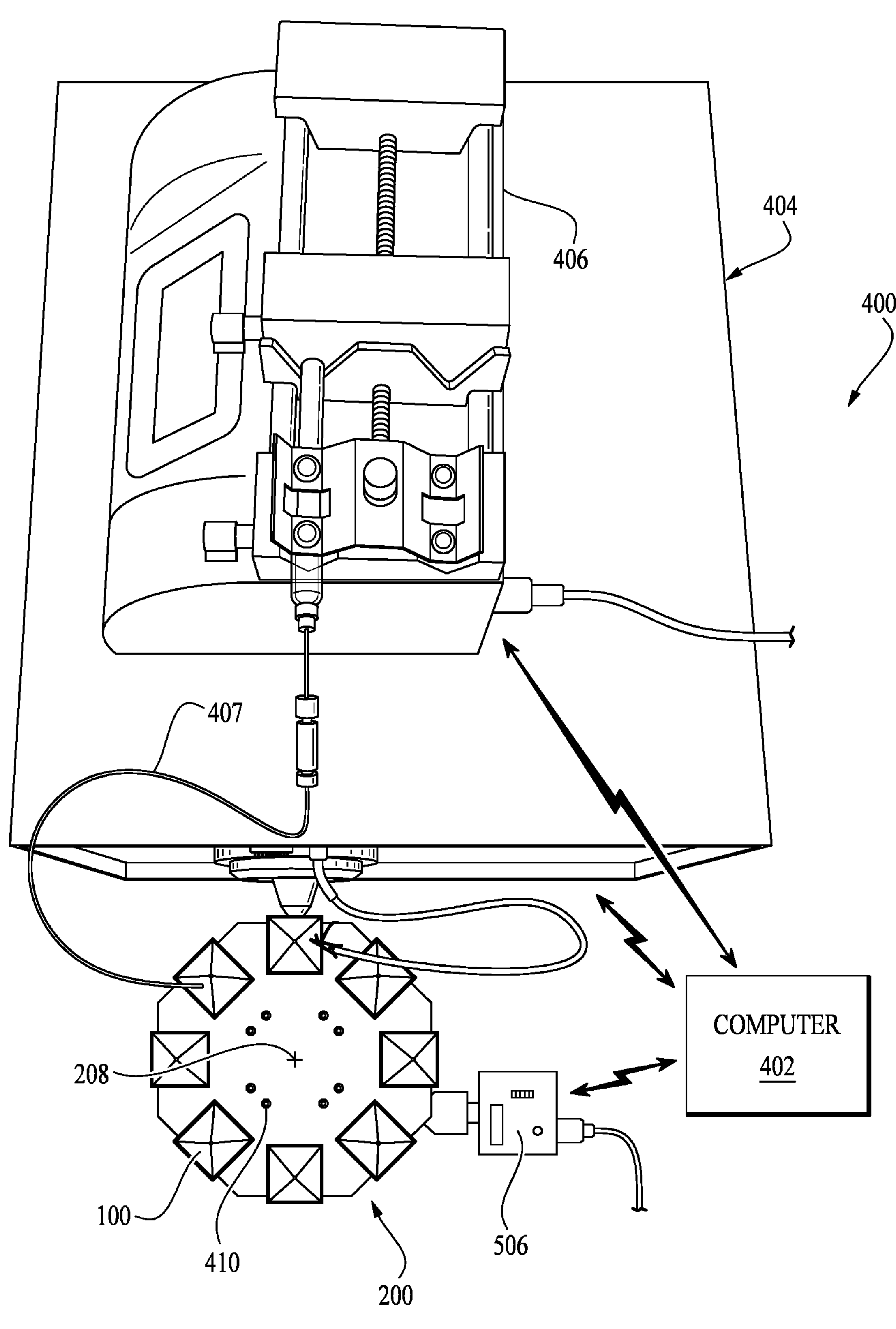
FIG. 4 illustrates a plan view of a sampling system, according to some embodiments.
Figure 5:
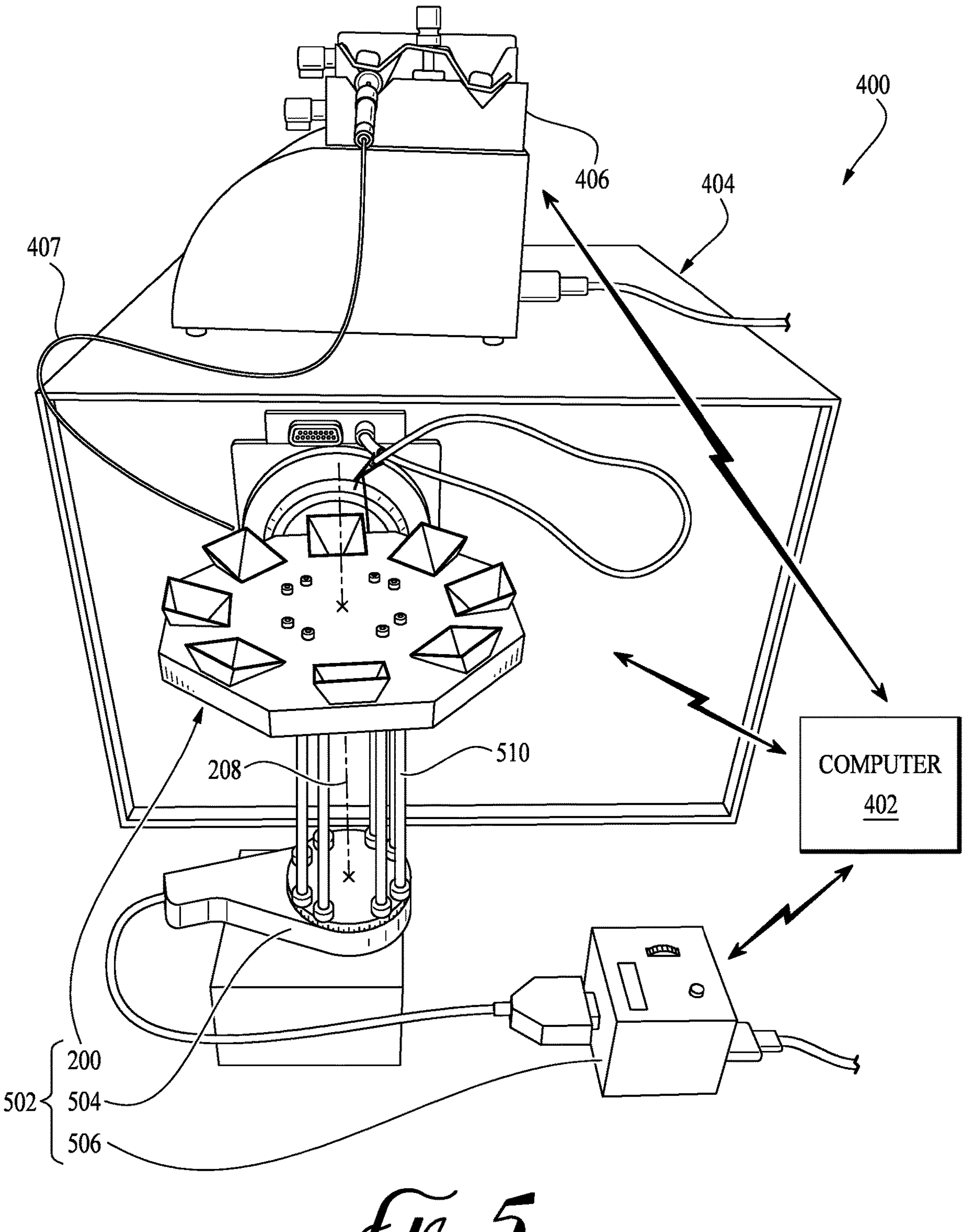
FIG. 5 illustrates an isometric view of the sampling system in FIG. 4.

The system embodiments in FIGS. 4 through 9 may refer to the platform 200 as rotary disc or rotary platform. FIG. 4 illustrates a plan view of a working sampling system 400. FIG. 5 illustrates an isometric view of the system 400. The system 400 includes a motorized platform 502, which is best viewed in its entirety in FIG. 5. The motorized platform 502 includes a rotary disc 200, an electric motor 504, and controller 506. The electric motor 504 can also referred to as a motor. A person having ordinary skill in the art will recognize that the apparatuses (i.e. platforms 200 from FIGS. 2A and 2B) can be used interchangeably in the system 400 for the rotary disc without detracting from the merits or generalities of the embodiments. The motorized platform 502 is configured with the rotary disc 200 electromechanically-coupled to the electric motor 504 and controller 506. A person having ordinary skill in the art will recognize that the electric motor 504 and controller 506 can also be a single component, such as a servo-controller or separate components without detracting from the merits or generalities of the embodiments. It is also understood that, should a user wish to do so, the rotary disc 200 could be manually-rotated into specific positions that would allow for analyses, without including or using the electric motor 504 and controller 506.

The rotary disc 200, has a first side 202, a second side 802, an outer edge 204, and a central longitudinal axis 208. Mounting holes 210 are shown in FIGS. 2A and 2B, as well in FIG. 2C. The mounting holes 210 are also used in the system 400 embodiments shown in FIGS. 4, 5, 6, and 8. The mounting holes 210 are used to secure the rotary disc 200 to the electric motor 504. The motor 504 used is a rotation stage platform and was the base for the rotary disc 200 for automated control. Eight mini-series adaptors with external M4 threads and internal M3 threads were inserted at equidistant positions in the mounting holes 210. Two mini-series optical posts, each having with a six millimeters diameter and a length of 75 millimeters, were screwed into each mini-series adapter to create eight posts 510 each about 150 millimeters tall. The posts 510, which can also be referred to as mounting posts or rods, attach the rotary disc 200 to the electric motor 504. M3 screws 410, each having a length of thirty millimeters, were threaded through the mounting holes 210 from the first side 202 to attach the rotary disc 200 to the posts 510 that were inserted through the mounting holes on the second side 802. The rotary disc 200, posts 510, and screws used for secure attachment can be adjusted based on the environment, including height requirements of the mass spectrometer 404 being used. It is understood that a different number of posts 510 can be used and that the sizes can be varied based on user discretion. Additionally, it is understood that various lifts, tables, stands, bars, and clamps are used for height and placement purposes based on environment conditions, i.e. laboratory versus use.

The system includes a computer 402 used for communicating with components. Communication links throughout the system 400 can be wireless data links, hard-wired, or a combination of the two depending on component capabilities. It is understood that the computer 402 includes a computer display screen, sometime referred to as a visual display screen or similar variation. The communication links are generically shown by jagged lines with arrows. The computer 402 is in communication with the motorized platform 502 and, in particular, the controller 506 to provide instructions to the controller. The controller 506 is configured to prompt the electric motor 504 to actuate, i.e. engage, based on received computer instructions. It should be noted that the computer 402 can be referred to as a non-transitory electronic processor readable medium. Based on this, the computer instructions are electronic processor executable instructions that, when executed by the processor, causes the processor to perform the processes described herein. It is understood that the computer 402 can be a desktop, laptop, tablet, or handheld computer such as, for example, a mobile phone, without detracting from the merits or generalities of the embodiments. It is also understood that a user can start the sample analysis using the system 400 by selecting an icon or executable file on the computer 402 such as, for example running a computer program. Additionally, it is also understood that the computer 402 includes a display screen for user viewing.

The computer 402 is also in communication with the mass spectrometer 404, via a dedicated internal mass spectrometer computer (not visible for ease of viewing and due to it being internal). The mass spectrometer 404 has a sampling inlet 902, which is illustrated in a close-up view in FIG. 9. The sampling inlet 902, is sometimes referred to as a mass spectrometer inlet or simply as the inlet, provides a vacuum. The system 400 includes a syringe pump 406, having a dedicated internal syringe pump computer (not visible for ease of viewing and due to it being internal). The computer 402 and syringe pump 406, via the dedicated internal syringe pump computer, are configured to communicate with each other. Both the dedicated internal syringe pump computer associated with the syringe pump 406 and the dedicated internal mass spectrometer computer associated with the mass spectrometer 404 can also be referred to as a non-transitory electronic processor readable mediums. Based on these aspects, the mass spectrometer 404 and the syringe pump 406 can communicate with each other in some embodiments via their dedicated internal computers, i.e. the dedicated internal syringe pump computer and the dedicated internal mass spectrometer computer. All communication in the system 400 both to and from the computer 402, both to and from the dedicated internal syringe pump computer, and both to and from the dedicated internal mass spectrometer computer can be referred to as electrical communication or as signal communication, which is strictly non-transitory signal communication.

The mass spectrometer 404 has an internal power source (not visible for ease of viewing and due to it being internal). The power source is configured to apply a high voltage as discussed below and can be referred to as a voltage source or high voltage source. All components in the system 400 such as, for example, the computer 402, the mass spectrometer 404, syringe pump 406, the electric motor 504, and controller 506, can be configured to access multiple power sources, including alternating current (AC) or direct current (DC), solar, wind, and generator power, with any required adaptor or transform techniques included. Additionally, mechanically-driven systems are included such as, for example, internal combustion engines, two and four-cycle engines, and tractor power take off shafts in place of the electric motor 504, without detracting from the merits or generalities of the embodiments.

Figure 8:
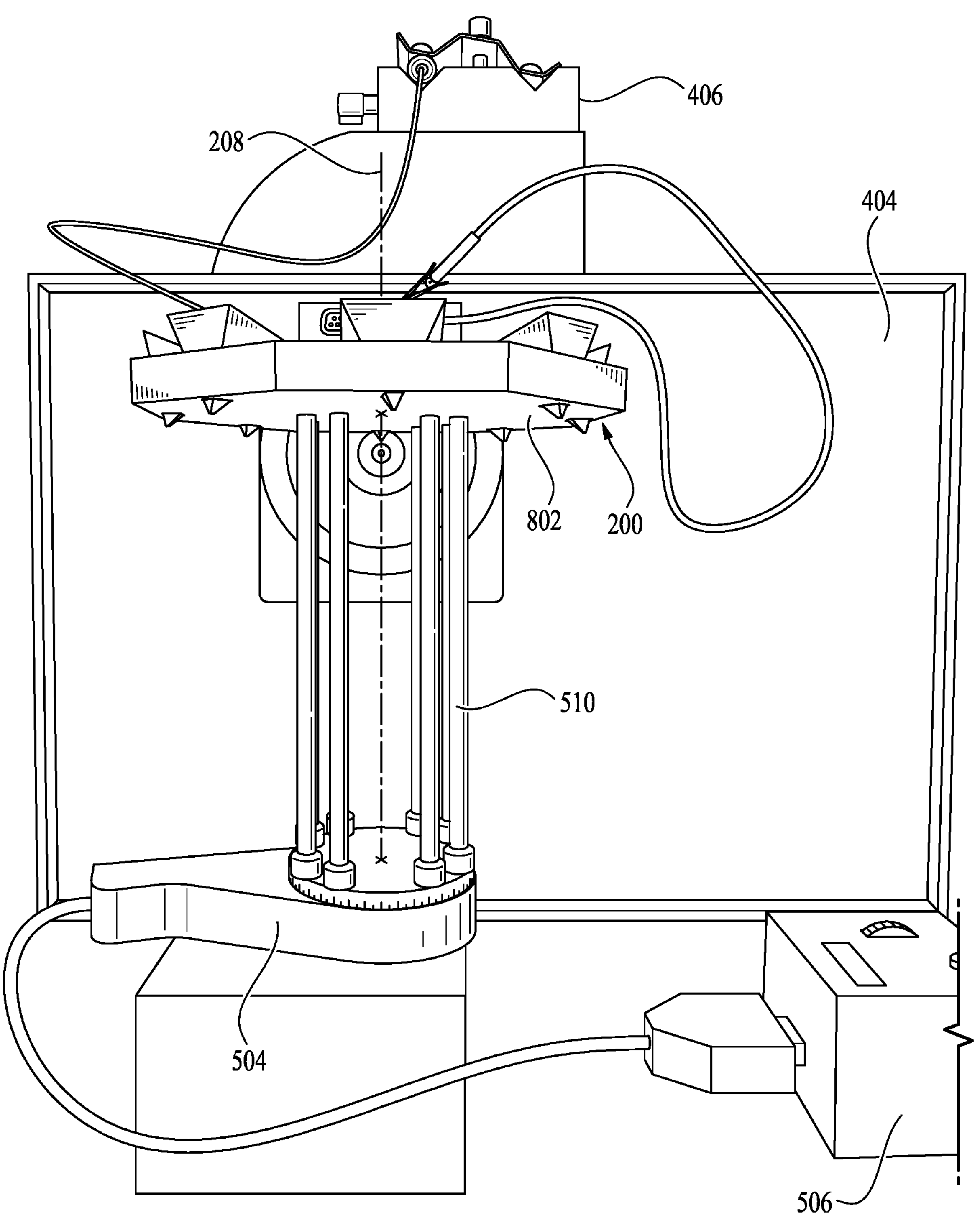
FIG. 8 illustrates an isometric view of the sampling system in FIG. 4 including a view of the underside of the sample collection apparatus.
Figure 9:
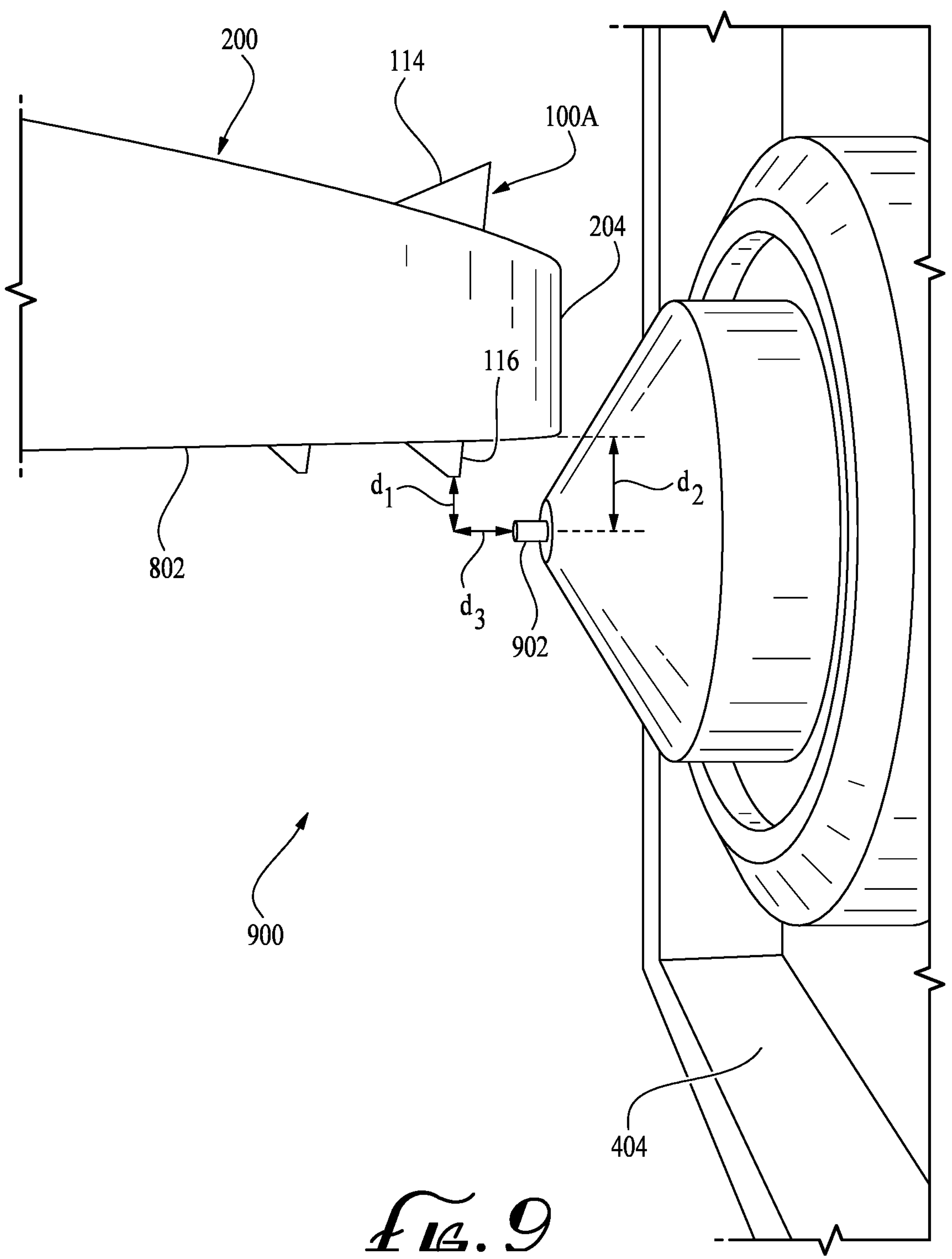
FIG. 9 illustrates a close-up side view of a portion of the sampling system in FIG. 4, illustrating the positioning and orientation of the sample collection apparatus and the distal end of the sample collection device in relation to the inlet of the mass spectrometer.

FIG. 8 allows one to view the underside of the sample collection apparatus 200. Referring simultaneously to FIGS. 4, 5, and 8, the plurality of receptacles 206 extend through the rotary disc 200 from the first side 202 to the second side 802 and are axially-spaced at equal distance about the central longitudinal axis 208. It is evident that the first side 202 can also be referred to as the top side or top surface. Similarly, the second side 802 can also be referred to as the bottom side or bottom surface. The plurality of receptacles 206 are apertures through the rotary disc 200. Each receptacle in the plurality of receptacles 206 is configured to removably-hold a sample collection device 100, sometimes referred to as a corresponding sample collection device.

Figure 6:
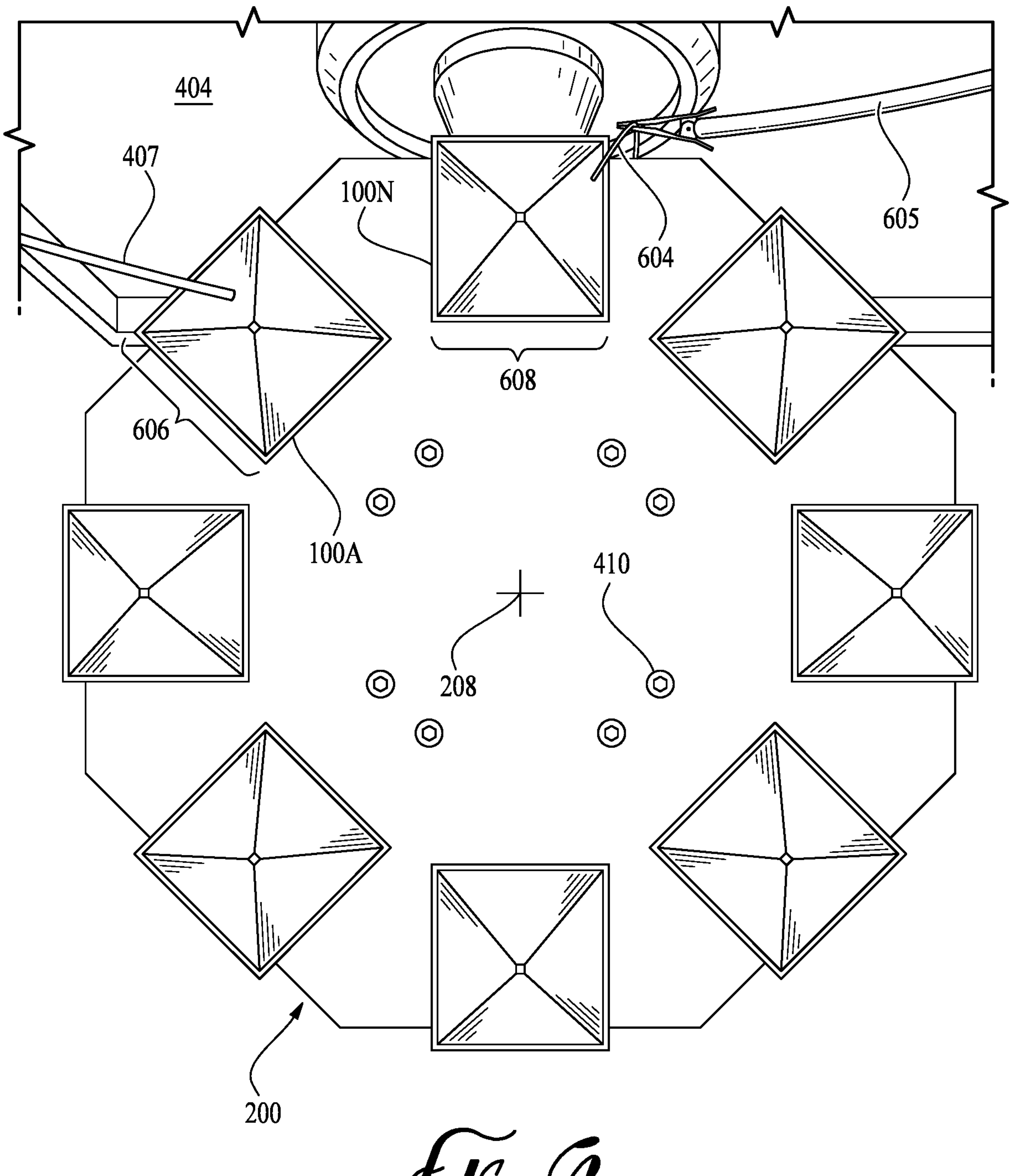
FIG. 6 illustrates a close-up plan view of the sample collection device in the sampling system in FIG. 4, including a solvent fill position and a high voltage application position.
Figure 7:
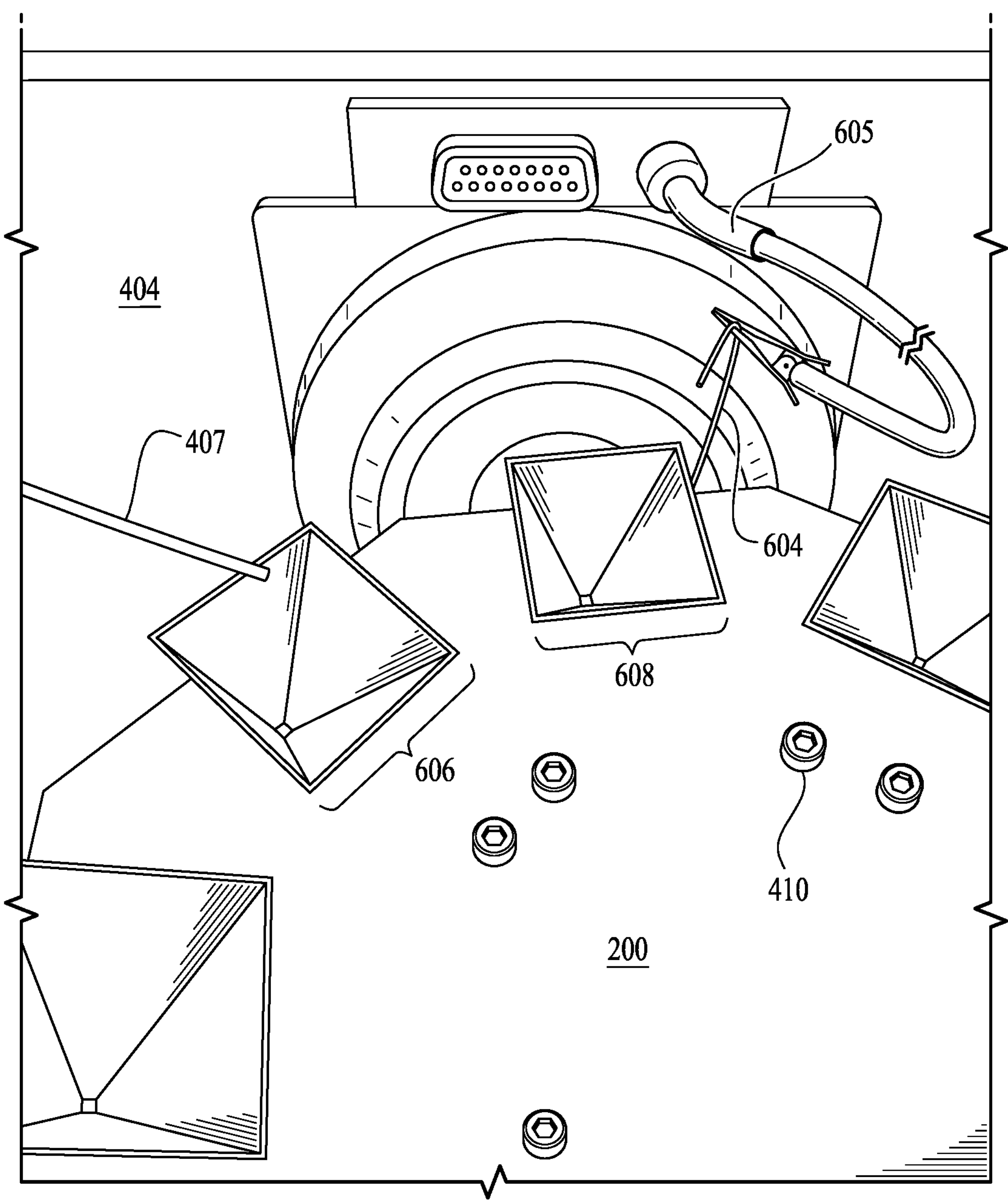
FIG. 7 illustrates a close-up isometric view of a portion of the sampling system in FIG. 4, including a close-up view of the solvent fill position and the high voltage application position, and the location of a connection to an internal power source in a mass spectrometer.

As shown in FIGS. 4, 5, and the close-up view in FIG. 6, each receptacle in the plurality of receptacles 206 has a dedicated sample collection device 100, which in the system environment 400, can be referred to as a corresponding sample collection device. The syringe pump 406 is in fluid communication with the each of the sample collection devices 100, i.e. in fluid communication with each corresponding sample collection device 100, based on the rotation and advancement of the rotary disc 200. A syringe hose 407 is connected to the syringe pump 406, providing the fluid communication from the syringe pump to the sample collection device 100 and enabling solvent to be deposited on the sample in the sample collection device.

Similarly, FIG. 6 depicts a wire 604 in contact with the proximal end 114 of the sample collection device. The wire 604 is electrically-connected to the mass spectrometer's 404 internal power source by an electrical cable 605. Thus, due to the sample collection device 100 being conductive and its proximal end 114 being in contact with the wire 604, the sample collection device is electrically-connected to the power source. By virtue of this connection, the mass spectrometer 404, through its power source, is configured to apply a high voltage to the sample collection device 100 in contact with the wire 604. One having ordinary skill in the art will understand that alternatives to the wire 604 exist to create a path for high voltage application. Some alternatives include providing a conductive portion such as, for example, using ball bearings embedded into the rotary disc 200 or having a conductive plastic portion or conductive plastic polymer portion in the rotary disc that contacts the sample collection device 100.

Referring to FIGS. 6 and 9, the sample in the sample collection device 100 to the left of the inlet 902 is defined as a solvent fill position 606, sometimes referred to as a first position, which is in fluid communication with the syringe pump 406 via the syringe hose 407. In the embodiments, the syringe pump 406 pumps solvent for ten seconds at a flow rate of six milliliters per minute to the first sample collection device 100A, which is positioned in the solvent fill position 606. Based on this, it is understood that the system 400 depicted will have eight total pulses of solvent, one for each time a sample collection device 100 is positioned in the solvent fill position 606.

Based on this, the system 400 shown in FIG. 4, upon beginning the analysis process, with all sample collection devices 100 in place and holding their respective samples, the rotary disc 200 begins with a first receptacle (the receptacle 206 counterclockwise to the inlet 902), holding a first sample collection device 100A, as shown in FIG. 6. The first receptacle holds the first sample collection device 100A, which is positioned in the first position 606, i.e. the solvent fill position. The syringe pump 406 is in fluid communication with the solvent fill position 606 and, at the beginning of the process, in fluid communication with the first sample collection device 100A.

A last sample collection device 100N is held in the voltage application position 608, or simply referred to as a second position, and corresponds with a last receptacle in the plurality of receptacles 206. The computer 402 instructs the controller 506 to actuate the electric motor 504 causing it to advance the rotary disc 200 about the central longitudinal axis 208. The advancement positions a next sample collection device at the first position 606. The computer 402 then instructs the syringe pump 406 to pump solvent into the next sample collection device. For reference, in FIG. 6, the next sample collection device is immediately counterclockwise to the first sample collection device 100A.

This advancement also causes the last sample collection device 100N to advance clockwise. It should be noted that, at this point, the last sample collection device 100N has not yet received solvent at the first position 606 and also did not receive high voltage at the second position 608. The computer instructs high voltage application of a sample collection device 100 only after the sample collection device has been in fluid communication, i.e. received solvent at the first position.

The advancement then positions the first sample collection device 100A at the second position 608, i.e. the high voltage application position. The power source is electrically-coupled with the first sample collection device 100A at the second position 608. The computer 402 instructs the mass spectrometer 404 to apply a high voltage from its internal power source to the first sample collection device 100A. The mass spectrometer 404 is always under vacuum and the sampling inlet 902, which is a metal, such as stainless steel, is exposed to the outside atmosphere. The high voltage application causes a voltage difference, sometimes referred to as a voltage differential between the first sample collection device 100A, which is at about four kV to about seven kV, and the sampling inlet 902, which is sometimes grounded and sometimes floated to approximately 100 volts (V) to 200 V. The voltage difference causes the solvent and resulting extracted products and its ions from the solid media sample containing the analyte to be sprayed into the sampling inlet 902. The vacuum from the mass spectrometer 404 is applied to the distal end 116 of the first sample collection device and assists with collecting the extracted products and its ions, but much less so than the voltage difference. The mass spectrometer 404 then analyzes the resulting extracted products from the first sample collection device 100A. The analysis determines the chemical composition and concentration of the resulting extracted products. It should be noted that the resulting extracted products, most importantly extracted analytes, are in liquid phase as they exit the distal 116 end of the first sample collection device 100A. However, due to the voltage difference, the extracted analytes are gas phase ions by the time they enter the mass spectrometer 404.

Analysis of samples in the system 400 continue by the advancement of the rotary disc 200 based on computer executable instructions stored on the computer 402. Thus, the pumping of solvent by the syringe pump 406 into sample collection devices 100 at the first position 606 continues. The high voltage application at the second position 608 continues for sample collection devices 100 that were previously in the first position 606 and received solvent from the syringe pump 406. The vacuum remains on. Extracted products are sprayed into the sampling inlet 902 and those extracted products are analyzed by the mass spectrometer 404. The process continues until all sample collection devices 100 have had their respective extracted products analyzed by the mass spectrometer 404.

Stated more simply, the process continues in such fashion that the rotary disc 200 continues advancing through all sample collection devices 100 from the first sample collection device 100A to the last sample collection device 100N, until: 1) the last sample collection device 100N has advanced to the first position 606 and received solvent from the syringe pump 606; 2) the last sample collection device 100N has advanced to the second position 608 and received the high voltage application and had its resulting extracted products sprayed into the sampling inlet 902; and 3) the mass spectrometer 404 analyzes the last sample collection device's 100N resulting extracted products.

Data obtained by the analysis can be shown and/or represented to a tangible medium for user verification, such as providing a visual verification to the user which could be useful before taking further action. Examples of the tangible medium include the display screen associated with the computer 402, hard copy printouts of data, as well as other media using the analysis data such as, for example, a computer having computer-readable instructions that is configured to use output from the embodiments.

Although eight sample collection devices 100 are depicted in the system 400, nomenclature for the first and last sample collection devices 100A and 100N is chosen to accommodate any number sample collection devices, hence the use of the "N" designation. The assigned number of N is equal to the number of sample collection devices 100, which is determined by the number of receptacles in the plurality of receptacles 206. Additionally, it is understood that nomenclature can be adapted upon actuation, i.e. rotation, of the rotary disc 200, so that the first sample collection device 100A then moves to the second position 608. The last sample collection device 100N then advances to eventually receiving solvent in the solvent fill position 606 and having high voltage applied in the second position 608.

The syringe pump 406 is configured to pump solvent to the first position 606 and then wait thirty seconds. For the process associated with the system 400 in FIG. 4, the rotary disc 200 rotates 45 degrees. This is based on the rotary disc 200 having eight receptacles 206 and, therefore, eight sample collection devices 100. A person having ordinary skill in the art will recognize, however, that the degrees of rotation can vary based on the diameter of the rotary disc 200, the axial-spacing about the central longitudinal axis 208 of the receptacles 206, and the number of receptacles. In many embodiments, rotation is a range of about 30 degrees to about 90 degrees. Solvent is then pumped to the first position 606 and high voltage is applied at the second position 608 to the proximal end 114. Analysis is performed by the mass spectrometer 404 for thirty seconds. Thus, after rotating, a thirty seconds waiting period is observed before the next rotation. It should be noted that the analysis time can vary, depending on application-specific conditions such as, for example, sample constituents and mass spectrometer type. Likewise, thirty seconds is an example and should not be construed as being limiting. As such, times greater than or less than thirty seconds can be used. The rotary disc 200 then rotates and the process continues until all sample collection devices 100 containing samples have been analyzed and their chemical compositions and concentrations determined.

The electric cable 605 can be referred to as a high voltage cable. The wire 604 can also be referred to as a high voltage wire. Various conductive clips, such as copper, can be used to connect the high voltage cable 605 to the wire 604. As the rotary disc 200 rotates to the next position, the sample collection device 100 that was in front of the inlet 902 comes in contact with the high voltage wire 604 and the high voltage is applied to the proximal end 114. The high voltage can be either positive or negative polarity depending on the analyte of interest, which is sprayed with the solvent into the inlet 902. This creates a Taylor cone. After all samples in the sample collection devices 100 have been analyzed, an analyst simply needs to replace used sample collection devices with new, unused sample collection devices. Should the sampling system 400 be operating continuously, the analyst would change the sample collection devices 100 before the mass spectrometer 404 completes its analysis of the sample in the last sample collection device 100N.

As shown in FIG. 6, the first sample collection device 100A is in a first position 606, which is often referred to as a solvent fill position. The syringe 406 then pumps solvent to the first sample collection device 100A and its associated solid media sample, i.e. the sample in the first sample collection device 100A. The rotary disc 200 when coupled to the electric motor 504 and controller 506, is configured to advance about the central longitudinal axis 208 upon instructions from the computer 402 sending computer executable instructions to the controller 506 and electric motor 504.

The advancement positions the first sample collection device 100A to the second position 608. The advancement causes the computer 402 to send computer executable instructions to the mass spectrometer 404 to apply a high voltage from the mass spectrometer's power source. The high voltage is applied to the proximal end 114 of the first sample collection device 100A after it advances to the second position 608. The mass spectrometer 404 applies a vacuum at its inlet 902. The amount of vacuum depends on the type of mass spectrometer 404 used and application-specific embodiments. In some embodiments, the high voltage applied is a range of 4 to 5 kV. In other embodiments, the high voltage applied is a range of 4 to 7 kV. While in other embodiments, the high voltage applied is a specific voltage such as, for example, 7 kV. Specific voltage levels and ranges are based on application-specific conditions and, as such, can be greater or less than that above voltage ranges.

FIG. 9 and reference character 900 depict the positioning of the first sample collection device 100A and the rotary disc 200 in relation to the mass spectrometer's inlet 902 after the rotary disc has rotated and placed the first sample collection device at the second position 608. For ease of viewing in FIG. 9, application of the high voltage to the proximal end 114 of the first sample collection device 100A is not shown. Positioning is such that as high voltage is applied, solvent and any resulting extracted products from the solid media sample are pulled through the hole 102 (not visible in the side view of FIG. 9) at the distal end 116 into the inlet 902, so that the mass spectrometer 404 can perform analysis.

Additionally, positioning assures unimpeded motion of the rotary disc 200 and sample collection devices 100 with objects such as, for example the mass spectrometer 404, while still allowing for a Taylor cone into the inlet 902. Appropriate positioning is controlled by the distal end 116 in relation to the inlet 902. In the embodiments, in the second position 608, the distal end 116 is five millimeters vertically (depicted as d1) above and five millimeters horizontally (depicted as d3) from the inlet 902, which is approximately a 45 degree angle. When properly positioned, the second side 802 of the rotary disc 200 is nine millimeters vertically (depicted as d2) above the inlet 902. As shown in FIG. 9, the outer edge 204, the second side 802, and the distal end 116 are unimpeded.

The positioning and spacing dimensions can be varied based on application-specific conditions. For instance, the depth that the sample collection devices 100 sit within the rotary disc 200 can be varied to control ion signal or concentration of analytes reaching the inlet 902. Based on this, the receptacles 206 can be optimized for trace and concentrated analytes by modifying the shape and dimensions of the inner walls 302.

System Embodiments—FIGS. 10 Through 12B

Figure 10:
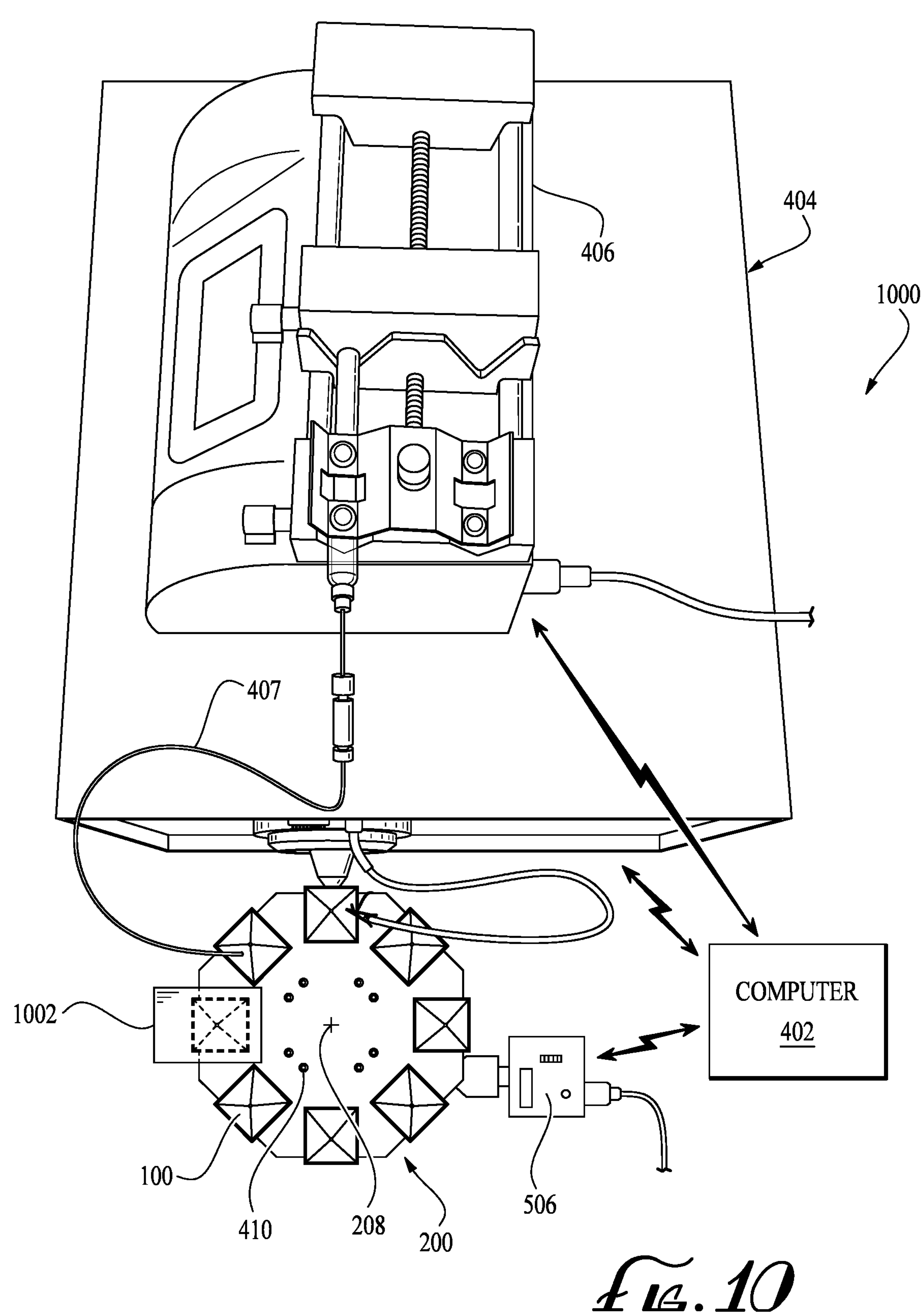
FIG. 10 illustrates a plan view of a system that couples a vibrational spectroscopy with the system in FIG. 4.
Figure 11:
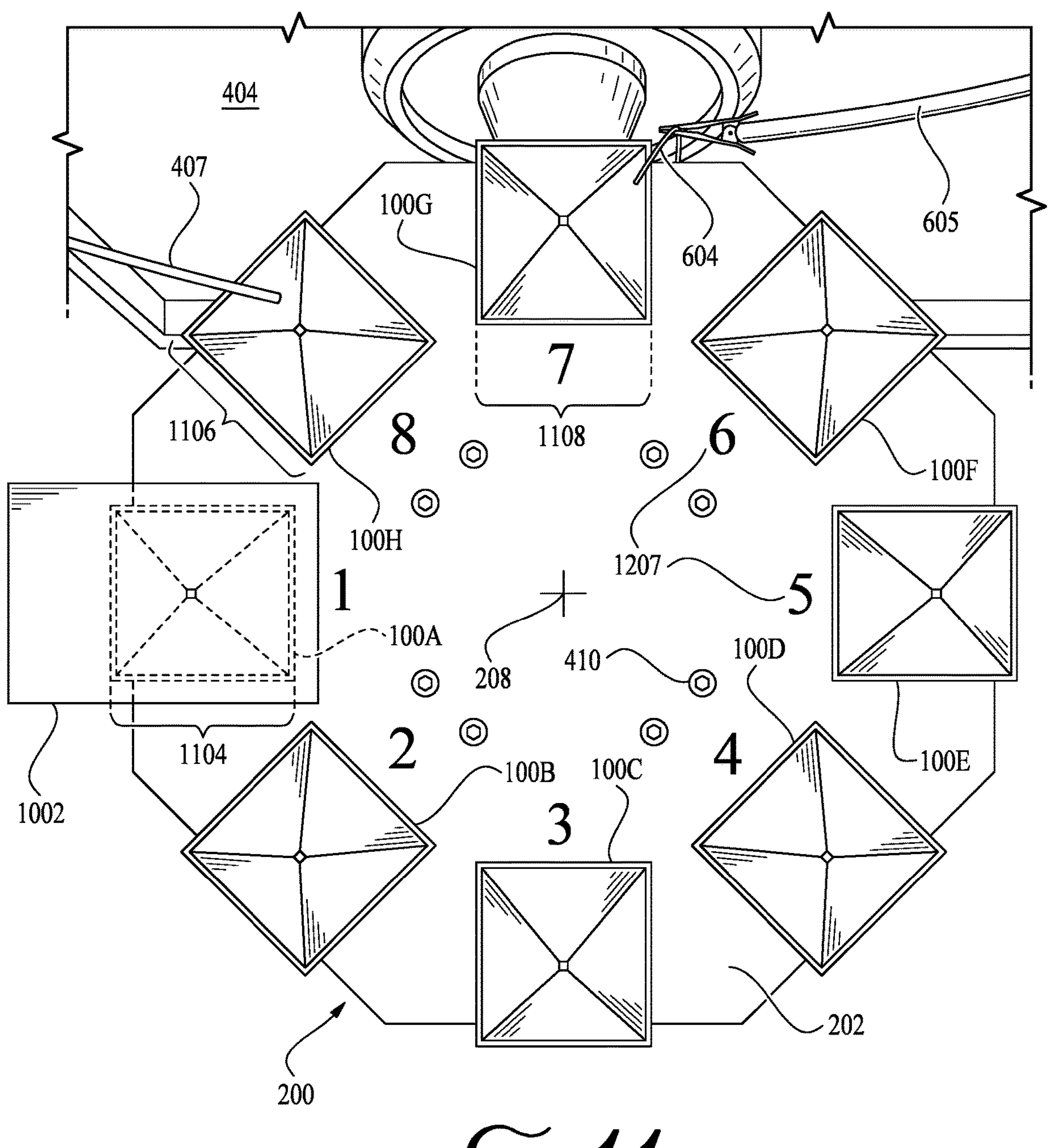
FIG. 11 illustrates a close-up plan view of the system in FIG. 10 and showing its sample collection apparatus, including a first position associated with vibrational spectroscopy, a second position associated with solvent fill, and a third position associated with high voltage application.
Figure 12A:
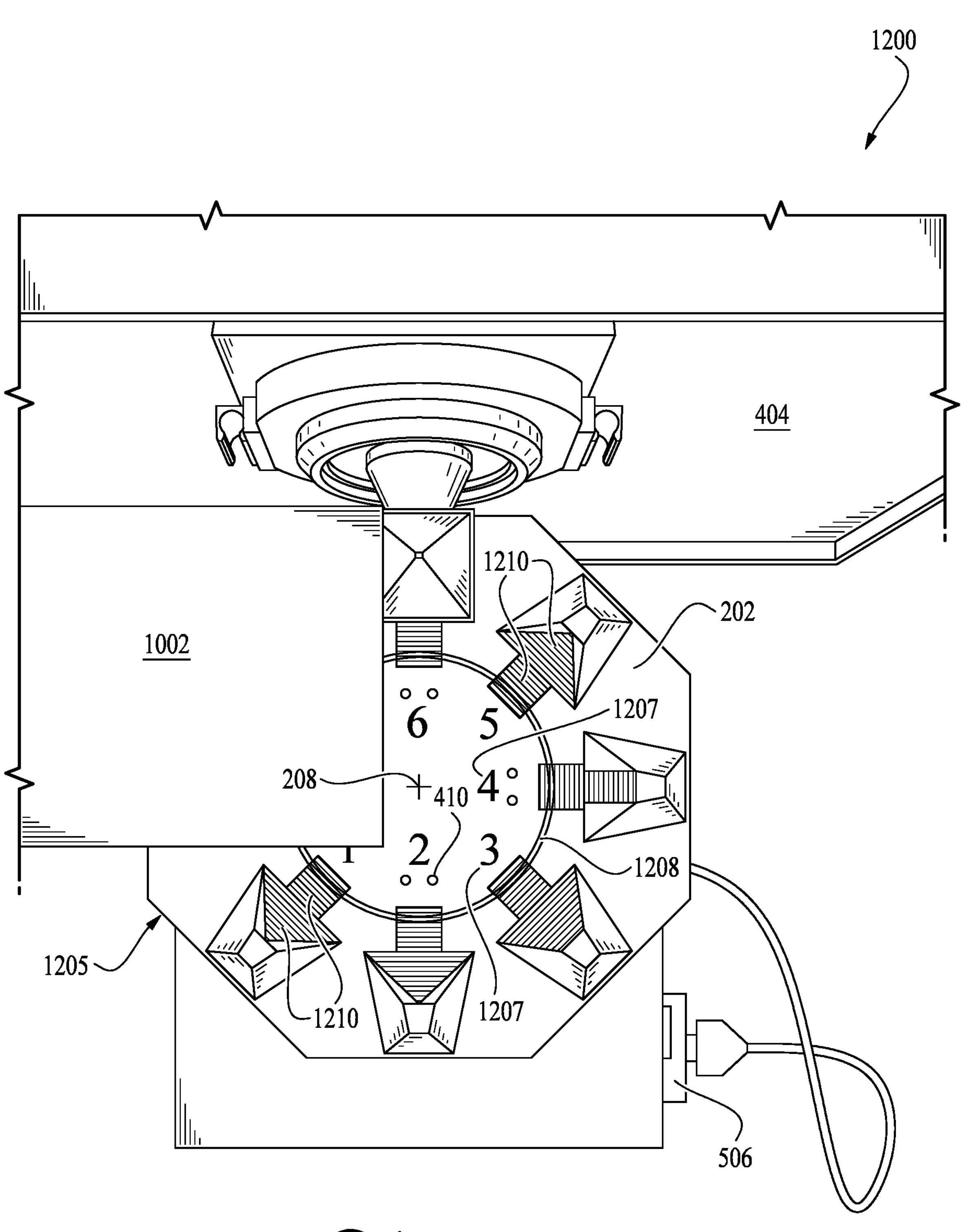
FIG. 12A illustrates a close-up plan view of an alternative system based on the system in FIG. 10 but introduces an alternative sample collection apparatus.
Figure 12B:
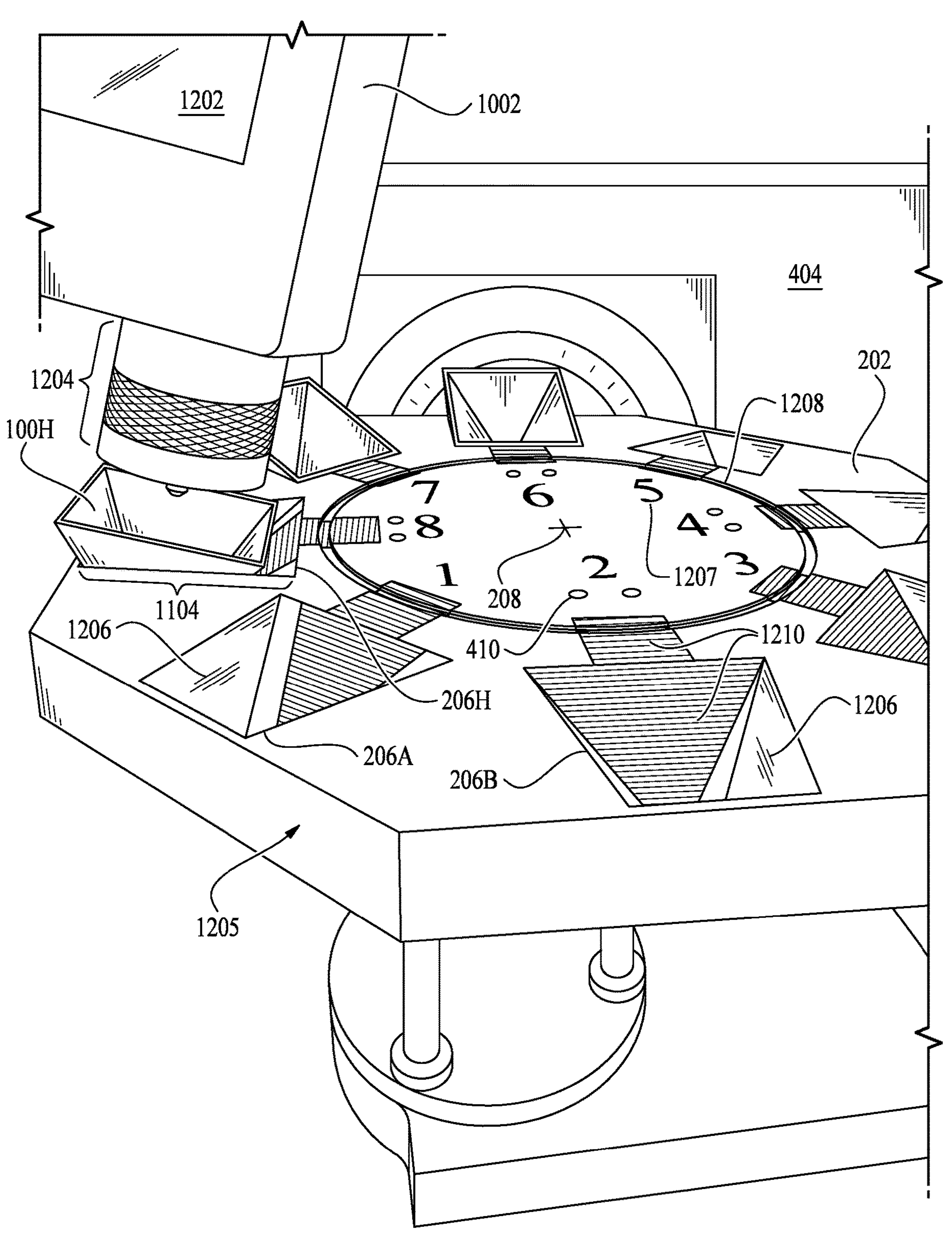
FIG. 12B illustrates a close-up side isometric view of the vibrational spectrometer and its orientation during vibrational spectrum collection associated with the first position in the alternative sample collection apparatus depicted in FIG. 12A.
Figure 13:
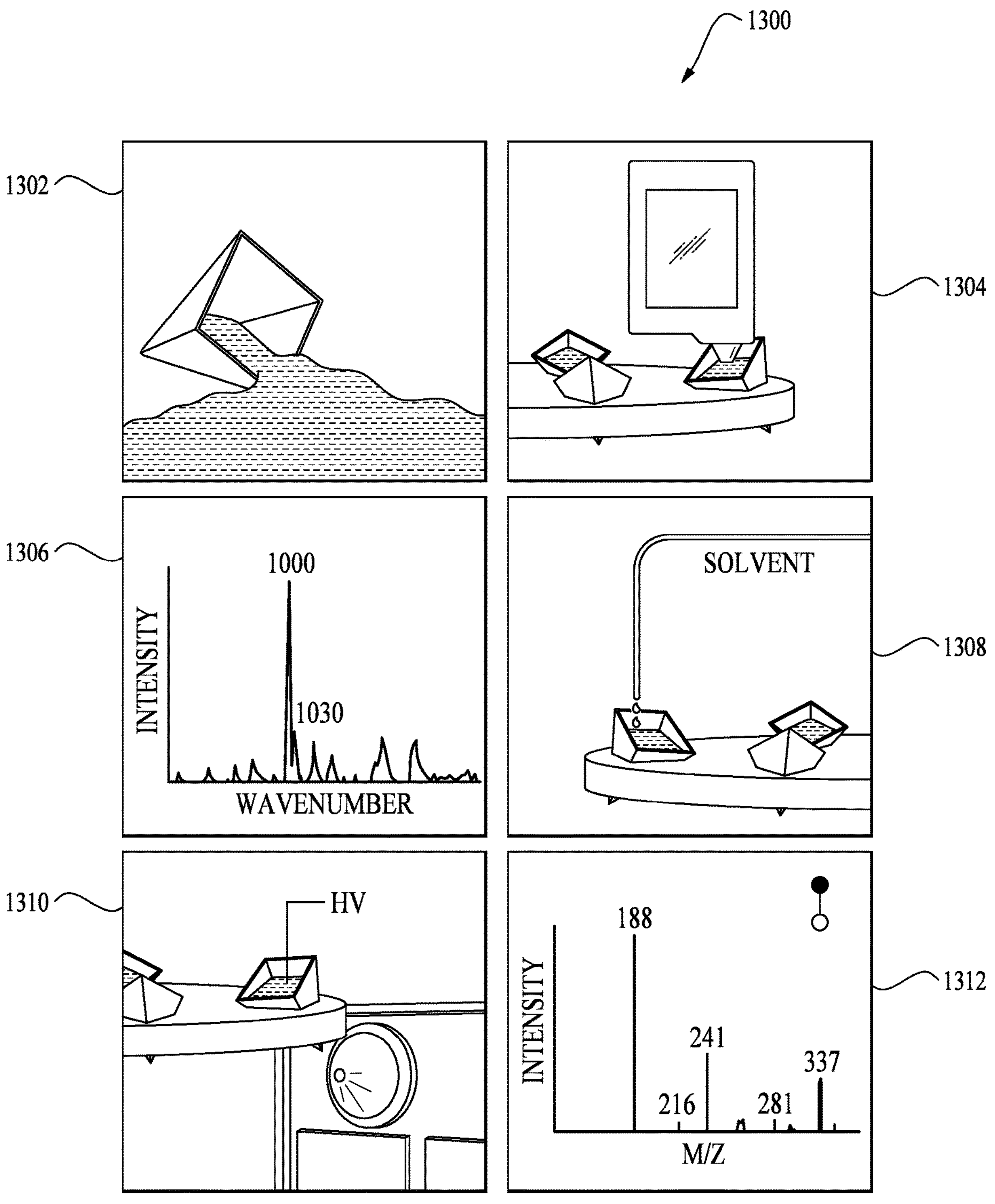
FIG. 13 illustrates a method of determining a solid media sample's chemical composition using the system in FIG. 10.

FIGS. 10 through 12B are directed to systems that couples vibrational spectroscopy to spray ionization mass spectroscopy. The system 1000 embodiments shown in FIGS. 10 and 11, as well as the system 1200 embodiments in FIGS. 12A and 12B, build upon the previous embodiments discussed, especially the system 400 in FIGS. 4 and 5. The systems depicted in FIGS. 10 and 11 (1000) and FIGS. 12A and 12B (1200) add an additional component—a vibrational spectrometer 1002, to enhance analysis, reduce or eliminate false positive results, and validate results. Method embodiments associated with the system 1000 in FIGS. 10 and 11, and the system 1200 associated with FIGS. 12A and 12B, are depicted in FIG. 13 and discussed in greater detail later.

Referring to the vibrational spectroscopy coupled to spray ionization mass spectrometry system 1000 in FIG. 10, the structural features depicted in FIGS. 1, 2B, 3, 4, 5, 8, and 9 and much of the associated discussion of those structural features are relied upon here. As such, not all features are discussed for the system 1000 in FIG. 10 or at least not discussed in the detail observed above due to the reliance mentioned. FIG. 10 depicts a plan view of the system 1000 that couples the vibrational spectrometer 1002, sometimes referred to as vibrational spectroscopy, with the system 400 depicted in FIGS. 4 and 5. One having ordinary skill in the art will recognize that the vibrational spectrometer 1002 can be a Raman spectrometer or an infrared spectrometer without detracting from the merits or generalities of the embodiments.

Referring to FIG. 10, and relying on FIGS. 4 and 5 for support, the system 1000 can also be referred to as a sampling and analysis system. The system 1000 can also be referred to as a system to determine an analyte's relative concentration or a system to determine a sample's relative concentration, or systems to determine the relative concentration of a solid media sample, which is accurate in all instances, including those where the sample does not contain an analyte. Other variations are, of course, possible without detracting from the merits or generalities of the embodiments. Moreover, the system 1000 is used to identify and confirm, i.e. validate the identification of the solid media sample's chemical composition and, if an analyte is present, determine the analyte's relative concentration.

Relying on FIGS. 4, 5, and 9, the system 1000 includes a motorized platform 502, a computer 402, a vibrational spectrometer 1002, a syringe pump 406, and a mass spectrometer 404. The motorized platform 502, which is best viewed in its entirety in FIG. 5, includes a rotary disc 200, an electric motor 504, and controller 506. The rotary disc 200, as mentioned earlier, can also be referred to as a sample collection apparatus. It is understood that one having ordinary skill in the art will recognize that the components in the system 1000 have access to an appropriate power source—either wall connection, battery, generator, or other source providing amble power required.

The vibrational spectrometer 1002 depicted in FIGS. 10 through 12B is a Raman spectrometer. The vibrational spectrometer 1002 is not physically attached to the rotary disc 200 but is instead held above it so that the sample collection device 100 aligns with the vibrational spectrometer which, in FIGS. 12A and 12B, is the detector, i.e. laser portion 1204 of the Raman spectrometer. Based on this, one having ordinary skill in the art will recognize that the vibrational spectrometer 1002 can be a Raman spectrometer or an infrared spectrometer without detracting from the merits or generalities of the embodiments. All wavelengths employed by common vibrational spectrometers, such as Raman and infrared spectrometers, are compatible with the embodiments. It is understood that the vibrational spectrometer 1002 is powered in similar fashion as the other components discussed herein.

Both the mass spectrometer and the vibrational spectrometer 1002 can be stationary or portable. When stationary, the term "benchtop" is commonly used such as what a person having ordinary skill in the art is familiar with in a laboratory environment. Examples include attaching the particular spectrometer to a stand or using a separate platform or table for support, as needed. As such, when the mass spectrometer 404 is stationary, such as in the laboratory environment, it can be referred to as a benchtop mass spectrometer. Similarly, when the vibrational spectrometer 1002 is stationary, such as in the laboratory environment, it can be referred to as a benchtop vibrational spectrometer. It is understood that the vibrational spectrometer 1002 can be handheld, such as a handheld Raman spectrometer or a handheld infrared spectrometer. Furthermore, one having ordinary skill in the art will understand how the various components used in the embodiments work, operate, and perform their respective analyses.

It is understood that when the vibrational spectrometer 1002 is handheld, it includes an integral visual display screen 1202 (partially shown in FIG. 12B). The vibrational spectrometer 1002 is configured with a detector 1204, which can be referred to as a detector inlet, and on a Raman spectrometer, shown in FIG. 12B, a laser portion. The vibrational spectrometer 1002 is configured to communicate with the computer 402, either by being hardwired to the computer or through wireless communication. Communication lines are not depicted for the communications between the vibrational spectrometer 1002 and the computer 402 for ease of viewing and to not clutter FIG. 10. It is understood that the communication between the computer 402 and vibrational spectrometer 1002 allows for the vibrational spectrum, such as the Raman spectrum when using a Raman spectrometer, to display the spectrum on the computer's 402 visual display screen or on the integral visual display screen 1202 associated with the vibrational spectrometer 1002.

The rotary disc 200 is electromechanically-coupled to the electric motor 504 and the controller 506. The rotary disc 200 depicted in FIG. 10 is based on the rotary disc in FIG. 2B, although the rotary disc in FIG. 2A can also be used. A plurality of receptacles 206 extend through the rotary disc 200 from the first side 202 to the second side 802. Each receptacle in the plurality of receptacles 206 is configured to removably-hold a sample collection device 100 (shown in FIG. 1).

The plurality of receptacles 206, as mentioned earlier, are axially-spaced at equal distance about the central longitudinal axis 208. The plurality of receptacles 206 could be designated mathematically as $R_1$ . . . . Rn, with n equal to four to twelve, indicating four to twelve receptacles. A person having ordinary skill in the art will recognize that the number of receptacles can exceed those limits based on application specific conditions. In FIGS. 10 through 12, eight receptacles 206 are depicted.

Each receptacle in the plurality of receptacles 206 has inner walls 302 (shown in FIG. 3) cooperating with the geometry of the sample collection device 100. It is understood that the sample collection devices 100 fit in the receptacles 206 and are held in place through either lost motion due to the geometry of the inner walls 302 (shown in FIG. 3), friction fit with the inner walls, the force gravity, or a combination of two or more of these.

The computer 402 is configured to communicate with the controller 506 and provide instructions to the controller. Upon receiving those instructions, the controller is configured to actuate the electric motor 504, thereby rotating the rotary disc 200, which advances the sample collection devices 100 to the first, second, and third positions 1104, 1106, and 1108, respectively, shown in FIG. 11. It is understood that, for purposes herein, the computer 402 is synonymous with an electronic processor and the computer instructions, sometimes referred to as processor or electronic processor instructions or computer executable instructions, that cause the actuation. Control of the systems 1000 and 1200 can be based on the computer executable instructions stored on the computer 402, coupled with user/operator actuation such as through the computer, switch, or wirelessly via a handheld computer or smartphone. Additionally, communication in the systems 1000 and 1200, both to and from the computer 402, including providing instructions, with any of the controller 506, mass spectrometer 404 via its dedicated internal mass spectrometer computer, the vibrational spectrometer 1002, the syringe pump 406, and any other computers that may be included, such as a user's smartphone, can be referred to as communication, transmission, electrical communication, signal communication, and similar variations. In all instances, the communication is strictly non-transitory signal communication.

Rotation of the rotary disc 200 can be either clockwise or counterclockwise, simply by reversing the electric motor 504 actuation, although the rotation is generally described herein as being clockwise to maintain consistency. The user can reverse the rotation if needed such as, for example, when a quick repeat analysis may be needed for the solid media sample in one of the sample collection devices 100. Rotation of the rotary disc 200 is described in significant detail below, especially with the actuation of the motorized platform 504. It is also understood that, should a user wish to do so or be required to do so, the rotary disc 200 could be manually-rotated or moved into specific positions that would allow for analysis to continue, without using the electric motor 504 and controller 506. Additionally, both the syringe pump 406 and the mass spectrometer 404 are configured to communicate with the computer 402 such as, for example, through hard-wire connection, wireless datalinks, and similar methods.

Each receptacle in the plurality of receptacles 206 is configured to receive or cradle the sample collection device 100. Stated another way, each receptacle in the plurality of receptacles 206 is configured to removably hold a corresponding sample collection device. This is best understood by viewing the plurality of receptacles 206 as distinct receptacles, i.e. first through eighth/last receptacles 206A through 206H, respectively, in both the rotary disc 200 and the rotary platform 1205. Based on this, it is apparent that the inner walls 302 of the receptacles 206 and the exterior surface of the sample container devices 100 are configured in complementary fashion to accommodate each other. Therefore, the first through eighth/last receptacles (206A through 206H) are configured to removably hold the plurality of sample collection devices 100, i.e. the first through last sample collection devices 100A through 100H, respectively, as depicted in FIG. 11.

In the FIG. 11 close-up plan view of the system 1000 from FIG. 10, the sample collection apparatus 200, i.e. the rotary disc, is visible. In the FIG. 12A close-up of an alternative system 1200, the system includes an alternative sample collection apparatus 1205, which can also be referred to as a rotary disc, platform, rotary platform, or an octagonal rotary platform since it has eight sides, and similar variations. As with the rotary disc 200 in FIGS. 10 and 11, the rotary platform 1205 in FIGS. 12A and 12B can also be considered substantially circular based on the context. In the FIG. 12B close-up side isometric view, the vibrational spectrometer 1002—a Raman spectrometer in this view, is shown during vibrational spectrum collection, i.e. Raman spectrum collection associated with the first position 1104. FIG. 12B is very useful for demonstrating the orientation and positioning of the Raman spectrometer 1002 and its detector 1204, i.e. laser portion, without regard to the particular rotary disc 200 or rotary platform 1205 or system used, especially because both the inner walls 302 of each receptacle in the plurality of receptacles 206, i.e. the first through eighth/last receptacles 206A through 206H, and each of the sample collection devices 100, i.e. the first through eighth/last sample collection devices 100A through 100H, are similarly configured to complement each other.

Referring simultaneously to FIGS. 11, 12A, and 12B, the rotary disc 200 (FIG. 11) and the rotary platform 1205 (FIGS. 12A and 12B) is labeled with numbers “1” through “8.” Reference character 1207 is used to refer to the numbers “1” through “8,” which are quick reference points and are graphical alert nomenclature for the user/operator. Other similar terms may be used herein for the graphical alert nomenclature 1207 such as, for example, graphical alert features, graphical alert nomenclature features, and similar variations. The graphical alert nomenclature features 1207 can be raised letters, numbers, or equivalent symbols that are vertically raised above the top surface 202, i.e. at a slightly higher elevation than surrounding features. Alternatively, the graphical alert nomenclature features 1207 can be engraved into the top surface 202 or have a different color than the surrounding features, or any combination that are visibly apparent to the operator. This is especially useful in the field when time is of the essence or pictures or videos are recorded to document analyses, which may be useful for documentary or evidentiary purposes.

Reference characters 100A through 100H represent individual sample collection devices and specific positions on the rotary disc 200. For instance, reference characters 100A, 100B, 100C, and 100D designate first, second, third, and four sample collection devices, respectively. Continuing, fifth, sixth, seventh, and eighth sample collection devices are depicted by reference characters 100E, 100F, 100G, and 100H, respectively. Reference character 100H can also generically be referred to as a last sample collection device. It should be noted that FIG. 11, as well as earlier FIG. 6, show the rotary disc 200 with all receptacles 206 containing their respective sample collection devices 100. However, it is certainly possible, even likely in some instances, that only a few, or even one sample collection device 100 may be placed in one receptacle 206 in the rotary disc 200, with the remaining receptacles 206 empty, i.e. the remaining receptacles not holding corresponding sample collection devices.

It is evident that the graphical alert nomenclature features 1207, i.e. the numbers “1” through “8” on the rotary disc 200, correspond with the first through eighth sample collection devices 100A through 100H, respectively, as well as the first through eighth or last receptacles 206A through 206H, further illustrating the embodiments' usefulness to the user/operator when time is of the essence.

Based on this nomenclature, and referring to FIGS. 2B and 11, the first receptacle 206A is configured to removably hold the first sample collection device 100A and the eighth/last receptacle 206H is configured to removably hold the eighth/last sample collection device 100H. It is evident that each of the remaining receptacles (second, third, fourth, fifth, sixth, and seventh receptacles 206B through 206G, respectively) are configured to removably hold the second through seventh sample collection devices 100B through 100G.

The rotary disc 200, as shown in FIG. 11, has three positions—a first position 1104, a second position 1106, and a third position 1108, with each position corresponding to a discrete process with the goal of determining the chemical composition of the solid media sample, especially regarding whether or not the solid media sample contains an analyte. Although not entirely depicted in FIGS. 12A and 12B, the same positioning and discussion, i.e the first, second, and third positions 1104, 1106, and 1108, respectively, and the analytical and validation processes and procedures also apply to the system 1200 when using the rotary platform 1205. The first position 1104 corresponds to collecting the vibrational spectrum using the vibrational spectrometer 1002 i.e., either the Raman spectrometer or infrared spectrometer. The second position 1106 corresponds to a solvent fill position from the syringe pump 406. A portion of syringe hose 407 is observed in FIG. 11, exhibiting fluid communication between the syringe pump 406 and the sample collection device 100 in the second position 1106 which in this instance as depicted in FIG. 11, is the last sample collection device 100H. It is understood by one having ordinary skill in the art that the syringe pump 406 has a sufficient solvent supply. Finally, the third position 1108 corresponds to a high voltage application and mass spectrum collection by the mass spectrometer 404.

After a solid media sample suspected of containing an analyte is collected, it is placed in a sample collection device 100. For purposes herein, the solid media sample is collected and placed in the first sample collection device 100A, with the first sample collection device residing in the first receptacle 206A (FIG. 2B). The first sample collection device 100A is shown with hidden lines because it is concealed in FIG. 11 by the vibrational spectrometer 1002 in this orientation, corresponding to the first position 1104. In FIG. 12B, the eighth, i.e. last sample collection device 100H is visible and is in the first position 1104, with the vibrational spectrometer 1002, i.e. the Raman spectrometer positioned for Raman spectrum collection.

The first sample collection device 100A is configured to hold the first solid media sample. The second sample collection device 100B is configured to hold the second solid media sample and continues in progression with the third sample collection device 100C through the last sample collection device 100H (the eighth sample collection device in FIG. 11) configured to hold the third through last solid media samples, respectively.

Referring to the close-up side isometric view of FIG. 12B, the vibrational spectrometer 1002 shown is a Raman spectrometer. As noted earlier, the structure and positioning shown in FIG. 12B regarding the vibrational spectrometer 1002 is applicable in all embodiments depicted in FIGS. 10 through 13. The vibrational spectrometer 1002 i.e., Raman spectrometer, shows its orientation during the vibrational spectrum collection which, in this instance, is the Raman spectrum collection. The Raman spectrometer 1002 depicted in FIG. 12B is a handheld unit and includes a visual display screen 1202, referred to above as the integral visual display screen, and its detector 1204, i.e. laser portion, to collect the Raman spectrum from the solid media sample in the first sample collection device 100A in FIG. 11 at the first position 1104. The difference in FIG. 12B compared to FIG. 11 is that the last sample collection device 100H is in the first position 1104 for Raman spectrum collection, illustrating a likely occurrence in a real-world scenario where operators are pressed for time and quick analysis is needed. This in no way deters from the merits or generalities of the embodiments. The Raman spectrum can then be displayed on the Raman spectrometer's visual display screen 1202, as well as being communicated to the computer 402, to be displayed on the computer's visual display screen if so desired. Additionally, the Raman spectrum can also be sent to other electronic devices such as, for example, smartphones.

Referring to FIG. 11, after the vibrational spectrum is obtained, the rotary disc 200 is rotated about its central longitudinal axis 208 to position the first sample collection device 100A at the second position 1106. When automated, the rotation is by instruction from the computer 402 to the controller 506 that provides instruction to the electric motor 504 to advance the rotary disc 200 in such fashion that the first sample collection device 100A is under the syringe hose 407 at the second position 1106 i.e., the solvent fill position. The syringe pump 406 is in fluid communication, via the syringe hose 407, with the respective sample collection device 100 at the second position 1106 which, in the first iteration, it is assumed to be the first sample collection device 100A. After prompting from the computer 402, the syringe pump 406 pumps solvent through the syringe hose 407 and into the first sample collection device 100A. This prepares the solid media sample in the first sample collection device 100A for the third position 1108.

After solvent is pumped into the first sample collection device 100A, the computer 402 instructs the controller 506 to prompt the electric motor 504 to actuate i.e., rotate, the rotary disc 200 about the central longitudinal axis 208. This positions the first sample collection device 100A at the third position 1108. FIG. 9 and its accompanying discussion is relied upon, especially with respect to positioning the sample collection device 100 which, in this iteration, is the first sample collection device 100A. High voltage is applied to the first sample collection device 100A as discussed earlier and the resulting products from the solid media sample is sprayed into the mass spectrometer's sampling inlet 902. The mass spectrometer 404 then proceeds with its analysis to determine the mass spectrum of the resulting extracted products. The mass spectrum of the resulting extracted products is provided to the user/operator on the visual display screen of the computer 404, as well as other methods including by transmitting to, for example, a smartphone or other electronic devices.

The alternative rotary platform 1205 in FIGS. 12A and 12B has additional structural features compared to the rotary disc 200 in FIGS. 10 and 11. As with the rotary disc 200 from earlier, and aside from conductive portions discussed below, the rotary platform is mostly made of nonconductive plastic, i.e. nonconductive polymers. The rotary platform 1205 in FIGS. 12A and 12B is an alternative embodiment of the rotary disc 200 from FIG. 2B. First, the inner walls 302 are shown as being ribbed i.e., having ribs 1206, sometimes referred to as serrations or grooves, to assist with providing friction to removably hold the sample collection devices 100. The ribs 1206 are on the four interior walls 302 of each receptacle in the plurality of receptacles 206 and are oriented perpendicular to the direction of insertion of the sample collection devices 100 into the receptacles, with the direction of insertion defined as being from the first side 202 to the second side 802. This is apparent in the FIG. 12B closeup, especially the first and second receptacles 206A and 206B.

Second, an axial groove 1208 is observed in FIGS. 12A and 12B in the rotary platform 1205, with the axial groove centered about the central longitudinal axis 208. The axial groove 1208 is cut into the first side 202 of the rotary platform 1205 and approximates a circle having a substantially constant radius about the central longitudinal axis 208. Stated another way, the axial groove 1208 is substantially circular and is centered about the central longitudinal axis 208. Third, the rotary platform 1205 includes conductive ball bearings (not shown for ease of viewing), such as stainless steel or other conductive metals, that are embedded in the axial groove 1208. Finally, FIGS. 12A and 12B depict conductive plastic polymer portions 1210, sometimes simply called conductive portions or conductive plastic portions.

The conductive portions 1210 shown in FIGS. 12A and 12B are made by 3D printing using a dual extruder printer. One of the extruders has the non-conductive plastic and the other has the conductive plastic. The conductive plastic, i.e. conductive polymer material that is used for the conductive portions 1210 is the same material as the sample collection devices. Alternative methods of constructing the conductive portions 1210 includes fabrication or coating methods to apply the conductive polymer to the rotary platform 1205. The conductive portions 1210 are located on at least a portion of one of the inner walls 302 of each receptacle in the plurality of receptacles 206. Moreover, the conductive portions 1210 can be located on a single inner wall 302 or multiple inner walls of each receptacle in the plurality of receptacles 206. The conductive portions 1210 extend radially inward toward the central longitudinal axis 208 and terminate approximately at the graphical alert nomenclature features (the numerals "1" through "8") 1207 on the rotary platform 1205.

The alternative structural features allow for the wire 605 (FIG. 6) to be repositioned to engage the conductive ball bearings in the axial groove 1208 instead of the top of the respective sample collection device 100 in the third position 1108. Upon rotation of the rotary platform 1205, the wire 605 will energize the conductive portion 1210 in the third position 1108, which then provides high voltage to the sample collection device 100 in the third position.

Theory of Operation and Working System—FIGS. 4 and 5

Using the embodiments includes preparing the sample collection devices 100 and inserting the sample collection devices into the receptacles 206. The sample collection devices 100 are filled with the sample, i.e. the solid media sample and any analyte contained in the solid media sample. Filling of the sample collection devices 100 can be done either before or after inserting the sample collection devices into the receptacles 206. Solvent is applied to the sample at the first position 606 and voltage is applied at the second position 608. Analysis of the sample is then performed at the second position 608 by the mass spectrometer 404 to determine whether an analyte is present or not present, i.e. whether an analyte is detected or not detected in the sample. When an analyte is detected, the mass spectrometer 404 determines the analyte's chemical composition and relative concentration.

The rotary disc 200 can move clockwise or counterclockwise, depending on the electric motor 504 configuration and application-specific conditions. For simplicity, however, rotational movement herein is described as clockwise. The rotary disc 200 moves in a clockwise manner, rotating 45 degrees after each sample is analyzed. Computer executable instructions stored on a nontransitory computer readable medium such as, for example, the computer 402, provide instructions for a thirty seconds mass spectrometer 404 analysis time.

The embodiments enable solvent to be applied prior to analysis in the "prep," i.e. the first position 606, and when the sample collection device 100 moves into the "spray," i.e. the second position 608, high voltage is applied to initiate the electrospray. The high voltage line is held above the sample collection device 100 that is aligned with the inlet 902 and makes contact with the proximal end 114 only when in the second position 608. Depending on the mass spectrometer 404, the solvent and the high voltage can either be applied by the mass spectrometer or the external syringe pump 406 and an external power supply (not shown in the figures). The duty cycle of the system 400, via the computer 402 or mass spectrometer 404, can be changed to allow additional extraction time (after solvent deposition) in the sample collection device 100 prior to analysis as needed.

The solvent is applied to the solid media sample and the high voltage is applied to the proximal end 114 of the sample collection device 100. The solvent extracts the analyte and separates the analyte from the solid media sample to the solvent within the sample. High voltage is applied to the sample collection device 100 to form a spray plume at the distal end 116 where the hole 102 is located. Voltage is applied based on application-specific conditions, which can be for up to thirty seconds. The analyte is ionized and its chemical composition and concentration are then determined by the mass spectrometer 404.

The solvent extracts the analyte within the solid media sample. Some examples of the solvent include methanol, ethanol, propanol, isopropanol, acetonitrile, water, water mixed with organic solvents, and combinations thereof. The amount of solvent varies depending on the size of the sample collection device 100 and the solid matrix. The amount solvent is directly proportional to the size of the sample collection device 100 (i.e., as the size of the sample collection device increases, so does the amount of solvent used). Similarly, to increase the amount of time a spray plume is being produced, more solvent may be added. In some embodiments, the solvent may be added sequentially (e.g., three 2 milliliters aliquots) or all at once (e.g., one 6 milliliters portion). In other embodiments, the solvent is added in aliquots ranging from about one milliliter to about two milliliters.

In some embodiments, an additive is used in conjunction with the solvent. The additive assists with the extraction of the analyte of the solid media sample. The additive is added to the solvent prior to adding the solvent to the solid media sample within the sample collection device to form a mixture of the solvent and additive. Some examples of the additive that may be used with the solvent include acetic acid, formic acid, ammonium acetate, and combinations thereof. The amount of additive differs based on the additive and solvent that is used. For example, a mixture of methanol as the solvent and one percent formic acid as the additive may be used.

Sample analysis includes determining a sample analysis, thereby determining whether an analyte is present in the solid media sample and, when present, the chemical composition and concentration of the analyte. Additionally, if multiple analytes are detected, the chemical composition and concentration of each analyte is determined. When no analyte is detected, it is reported as no analyte detected or similar designation. Analyte presence, chemical composition, and concentration are determined by analyte standards of the molecule of interest. For example, if the data from the sample matches the standard, the target analyte is present. The mass spectrometer 404 performs the analysis using known techniques. The embodiments result in about sixty samples being examined in the same time as one sample is examined for liquid chromatography mass spectrometry (LC-MS).

After sampling the sample in a sample collection device 100, the rotary disc 200 advances to the next position where the used sample collection device is removed and a new sample collection device is now aligned with the inlet 902. The new sample collection device 100, i.e. solvent has been applied to the first sample collection device 100A, which is now in the second position 608 and in contact with the wire 604 providing high voltage, which initiates an electrospray (the Taylor cone) into the inlet 902 for sample analysis. Rotation occurs and the next sample collection device 100 is moved into the first position 606, i.e. the "prep" position and has solvent applied. Rotation is continuous and customizable to the number of samples needing analysis. The sample collection devices 100 that have already been analyzed do not need to be removed right away but should be replaced if the system 400 is set to continuously sample. For the system 400 shown in FIG. 4, eight sample collection devices 100 are used, which means that the sample collection devices would need to be replaced at least every six analyses to ensure no repetitive analyses. Increasing the diameter of the rotary disc 200 and ultimately the number of receptacles 206 can add to the amount of samples run during each cycle and increase the time in between sample removal and loading. Additionally, the operator can stop the analysis, i.e. rotation, at any time if needed or if it is determined that no additional analysis is needed or if enough information, such as evidence, is obtained.

Rotation of the rotary disc 200 can be controlled by a timer and be on a continuous loop based on instruction from the computer 402 or be triggered by a contact closure signal from the mass spectrometer 404. Similarly, once positioned the start-up of the sequence of solvent and high voltage application can be controlled by the computer 402 using a timer or be triggered by a contact closure signal from the mass spectrometer 404.

In some embodiments, the sample collection device 100 may be cleaned and reused in the field or at the laboratory to obtain another solid media sample. In other embodiments, the sample collection device 100 is discarded after sample collection. When the sample collection device 100 is cleaned and reused, the solid media sample is removed from the sample collection device and the sample collection device is submerged and sonicated in a solvent. The submerging and sonication step is repeated until the sample collection device 100 is cleaned (i.e., a clean standard sample is run with the sample collection device 100, which shows no chemicals present). In some examples, different solvents are used to clean the sample collection device 100 each time the sample collection device 100 is submerged and sonicated.

Theory of Operation, Working System, and Method Embodiments—FIGS. 10 Through 13

FIG. 13 depicts yet another embodiment—a method 1300 of using the system 1000 in FIG. 10. Specifically, FIG. 13 pictorially depicts the tasks used to determine a solid media sample's chemical composition, i.e. identifying the solid media using the system 1000 discussed above and shown in FIG. 10. Of particular interest in the method 1300 is whether or not the solid media sample is identified as containing an analyte and, if so, determining the analyte's relative concentration.

The method 1300 includes outputting and validating the results obtained in a tangible medium. An alert system can be utilized based on application-specific conditions such as, for example, when at least one analyte is identified and/or confirmed, or simply when a benign substance is identified and/or confirmed. FIG. 13 includes x-y graphs to illustrate the determination of various spectra discussed later. One having ordinary skill in the art will recognize that the x-y graphs depicted are for illustration only and should not be construed as being an exact rendering of a specific substance or analyte.

Referring to FIGS. 10 and 13 simultaneously, the method 1300 of determining whether a solid media sample has an analyte and its relative concentration, as well as outputting and validating the results, begins by providing the system as shown in FIG. 10 and depicted by reference character 1000. It should be noted that the description of the method 1300 is generally applicable to both the FIGS. 10 and 11 system 1000 as well as the FIGS. 12A and 12B system 1200. However, for simplicity, most of the method 1300 description will focus on FIGS. 10 and 11, with reliance as needed from FIGS. 12A and 12B.

The system's 1000 components are configured to determine a vibrational spectrum and a mass spectrum. This includes a motorized platform 502 having a rotary disc 200, an electric motor 504, and a controller 506. The system components also include a computer 402, a syringe pump 406, a mass spectrometer 404, and a vibrational spectrometer 1002. The specifics of the system 1000 and its structural features are discussed in great detail above in relation to FIGS. 10 through 12B and, as such, that detail is relied on here as much as possible. The description herein often describes the rotary disc 200 as advancing from one position to the next. In this context, a person having ordinary skill in the art will recognize that the advancement is rotation of the rotary disc 200 about the central longitudinal axis 208.

After the system 1000 is provided, a user or analyst executes task 1302. The solid media sample containing an analyte or suspected of containing an analyte is collected. Stated another way, the solid media sample is collected to determine whether it contains an analyte and, if it does contain an analyte, determine the chemical composition and relative concentration of the analyte. Or even more simply, the solid media sample is collected to determine its chemical identification, i.e. composition. Therefore, the embodiments can readily distinguish a benign substance such as, for example, flour or baking soda, from substances containing concerning chemicals, i.e. illegal or dangerous substances.

For simplicity, it is assumed here that the collection of the solid media sample begins with the first sample collection device 100A. Thus, task 1302 includes that the sample collection device 100 that is the first one placed in any receptacle 206, i.e. regardless of which receptacle it is, is defined for the method 1300 as being the first sample collection device 100A. Additional sample collection devices, i.e. the second through eighth/last sample collection devices 100B through 100H, can be used to collect additional solid media samples for analyses. A person having ordinary skill in the art will recognize that only one sample collection device is needed to demonstrate the functionality of the process.

The collection method can include using a single or several sample collection devices 100 to scoop the solid media sample such as, for example, as one would use a small shovel or trowel. Alternatively, other methods could also be used including, but not limited to, pouring solid media samples into the sample collection device(s) 100, using small shovels or spoons to pour solid media samples into the sample collection device(s), or using other methods that collect and then transfer the solid media samples into the sample collection device(s). For purposes herein, it is assumed that the solid media sample that is collected will be deposited, placed, or poured into the first sample collection device 100A. Additional solid media samples, i.e. additional samples, would then be placed in subsequent sample collection devices—the second through eighth/last sample collection devices 100B through 100H, if needed.

After collection, task 1302 includes placing the first sample collection device 100A holding the collected solid media sample in one the receptacles in the plurality of receptacles 206. It is advantageous to place the first sample collection device 100A in the first receptacle 206A, which is what FIG. 11 depicts, but it is not strictly required. Functionally, it is understood that the first sample collection device 100A could be placed in a different receptacle than the first receptacle 206A. This is more or less shown in FIGS. 12A and 12B where the first receptacle 206A is empty, i.e. does not contain the first sample collection device 100A or, for that matter, any sample collection device. However, for tracking purposes it is advantageous, although not required, to maintain an accurate method to document and record the analysis. This includes utilizing the graphical alert nomenclature features 1207 (the numbers "1" through "8" on the rotary disc 200 in FIG. 11), therein placing the first sample collection device 100A in the first receptacle 206A.

Included in Task 1302 is that the placement removably secures the first sample collection device 100A and any others that are also placed into any of the receptacles 206. In this context, the first sample collection device 100A is held in place in the first receptacle 206A in such fashion that when the rotary disc 200 is configured as disclosed in the embodiments, the first sample collection device is removably-secured and has a very low likelihood of falling out or being blown out from wind, especially when containing the solid media sample. The securing method can include friction fit, lost motion stop, and reliance on gravity, all of which are benefited by the configuration of the inner walls 302 as previously described. This also is applicable to subsequent sample collection devices such as, for example, the second through eighth/last sample collection devices 100B through 100H.

Referring to task 1304, the desire is that the first sample collection device 100A be placed in the first receptacle 206A, and that the rotary disc 200 be oriented so that this placement occur so that the vibrational spectrometer 1002 be able to immediately begin its analysis. In practice, however, that may not occur as noted above. In those situations where the orientation does not allow for that initially, the controller 506 is instructed to actuate the electric motor 504 to advance the rotary disc 202 about the central longitudinal axis 208 to position the first sample collection device 100A at a first position 1104, corresponding to the position of the vibrational spectrometer 1002. It is understood to a person having ordinary skill in the art knows how vibrational spectrometers 1002, including both Raman and infrared spectrometers, operate, and is able to properly position the devices at the correct orientation and distances needed for vibrational spectrum collection. As such, the orientation of the vibrational spectrometer 1002, i.e. the Raman spectrometer in FIG. 12B, and its detector 1204, i.e. laser portion, is oriented, positioned, and set at the necessary distance above the solid media sample as needed to collect the vibrational spectrum.

Task 1306 includes collecting, sometimes referred to as obtaining or determining, the vibrational spectrum. When using the handheld Raman spectrometer 1002 or another handheld spectrometer, i.e. an infrared spectrometer, the spectrum is displayed on a visual display screen 1202, i.e. the vibrational spectrometer's (Raman spectrometer in FIGS. 12A and 12B) visual display screen. It is understood by one having ordinary skill in the art that Raman spectrometers are associated with Raman spectra and infrared spectrometers are associated by infrared spectra. If desired, the vibrational spectrometer 1002 can transmit the vibrational spectrum to the computer 402 to be displayed on the computer's visual display screen. The user/operator/analyst can choose to view the spectrum on the either the vibrational spectrum's visual display screen 1202 or the visual display screen associated with the computer 402. In either instance, the vibrational spectrum is displayed on a tangible medium. For the display of the vibrational spectrum, the tangible medium can include the vibrational spectrometer's visual display screen 1202, i.e. the Raman display screen, the visual display screen associated with the computer 402, or both. When more than one tangible medium is used, the tangible medium displaying the vibrational spectrum can be referred to as a first tangible medium.

In task 1308, the computer 402 instructs the controller 506 to actuate the electric motor 504 to advance the rotary disc 200 about the central longitudinal axis 208 to position the first sample collection device 100A at a second position 1106. The second position 1106 corresponds to a solvent fill position. The computer 402 then provides instructions to the syringe pump 406 to pump solvent through the syringe hose 407 and into the first sample collection device 100A. This prepares the first sample collection device 100A for the third position 1108.

Referring to task 1310, the computer 402 provides instructions to the controller 506 to actuate the electric motor 504 to advance the rotary disc 200 about the central longitudinal axis 208 to position the first sample collection device 100A at a third position 1108. In the third position 1108, the distal end 116 of the sample collection device, which is the first sample collection device 100A in this iteration, is aligned and positioned with the mass spectrometer 404 and its sampling inlet 902. At the third position 1108, the mass spectrometer's power source is electrically-coupled with the first sample collection device 100A.

In task 1310, the mass spectrometer 404 also applies a high voltage (shown generically as "HV" in FIG. 13) from the power source to the first sample collection device 100A. The high voltage causes the solvent and its resulting extracted products from the solid media sample and any analytes present to be sprayed into the sampling inlet 902. In Task 1312, the mass spectrometer 404 then analyzes and determines, sometimes referred to as "collects," the mass spectrum of the resulting extracted products from the first sample collection device 100A. This determines the mass spectrum of the first solid media sample in the first sample collection device 100A and provides the user with the chemical composition, i.e. the solid media sample's identification, and if analyte(s) are present, the relative concentration of the analyte(s).

It is apparent that the rotary disc 200 for the system 1000 in FIGS. 10 and 11 moves in a clockwise manner, rotating 45 degrees between positions, i.e. the first, second, and third positions 1104, 1106, and 1108, based on there being eight receptacles 206A through 206H holding, at the most, eight sample collection devices 100A through 100H. However, it is apparent to one having ordinary skill in the art that the rotation degrees are based entirely on the number of sample collection devices 100 and receptacles 206.

Timing sequences and analyses in the embodiments are controlled by computer executable instructions stored on a nontransitory computer readable medium such as, for example, the computer 402. Using the first sample collection device 100A as an example, an approximate thirty seconds vibrational spectrometer 1002 analysis time is assumed, however it can be greater than that. After thirty to forty-five seconds of vibrational spectrometer 1002 analysis, the rotary disc 200 rotates to the second position 1106, where the syringe pump 406 then pumps solvent for ten seconds at a flow rate of six milliliters per minute to the first sample collection device 100A. Based on this, it is understood that the system 400 depicted will have eight total pulses of solvent, one for each time a sample collection device 100 is positioned in the second position 1106, i.e. the solvent fill position. After an approximate thirty to forty-five seconds allowed for solvent fill, the rotary disc 200 rotates and positions the first sample collection device 100 at the third position 1108 for high voltage application. The voltage application, from 4 kV to 7 kV, is applied for up to thirty seconds, based on application-specific conditions. The mass spectrometer 404 collects the mass spectrum, which is usually an approximate thirty to forty-five seconds analysis time.

Rotation of the rotary disc 200 can be controlled by a timer and be on a continuous loop based on instruction from the computer 402 or be triggered by a contact closure signal from the mass spectrometer 404. Similarly, once positioned the start-up of the sequence of solvent and high voltage application can be controlled by the computer 402 using a timer or be triggered by a contact closure signal from the mass spectrometer 404. Additionally, the operator can stop the analysis, i.e. rotation, at any time if needed or if it is determined that no additional analysis is needed or if enough information, such as evidence, is obtained.

Task 1310 includes outputting the mass spectrum in a tangible medium. This can include transmitting the mass spectrum from the mass spectrometer 404 to the computer 402 and displaying the mass spectrum on the computer's visual display screen. It could also include displaying the mass spectrum on the mass spectrometer's visual display screen, if so equipped. It could also include transmitting the mass spectrum to a user's smartphone. When more than one tangible medium is used, the tangible medium displaying the mass spectrum can be referred to as a second tangible medium. For example, the vibrational spectrum discussed earlier could be displayed on the first tangible medium and the mass spectrum could be displayed on the second tangible medium. Other variations are, of course possible, without detracting from the merits or generalities of the embodiments.

It should be noted that the x-y graphs in tasks 1306 and 1312 are prepared for the reader's convenience to pictorially illustrate the vibrational spectrum and mass spectrum, respectively, and should not be construed as illustrating a particular substance match or non-match. The vibrational spectrum (task 1306) displays the wavenumber on its x-axis and the intensity on its y-axis. The mass spectrum (1312) displays the mass to charge, shown as m/z on its x-axis and displays intensity on its y-axis. A person having ordinary skill in the art will recognize that the wavenumber is 1/wavelength, which is generally denoted with units $cm^{-1}$. Similarly, one having ordinary skill in the art will recognize that intensity is unitless.

For confirmation, validation, or verification purposes, the user/operator can compare the vibrational spectrum to the mass spectrum to determine that the substance either is a problematic substance or not. This can occur any number of ways. First, it could be a visual comparison of the two spectra such as, for example, comparing the vibrational spectrum (the Raman spectrum when using a Raman spectrometer) displayed on the Raman spectrometer's visual display screen 1202 with the mass spectrum on the computer's visual display screen.

Second, both spectra could be transmitted to a separate computer, such as a laptop computer or smartphone, for the spectra to be visually displayed and compared. Third, and a very likely way, is to make use of a commercial-off-the-shelf internal database and a commercial-off-the shelf computer program, both of which are stored on the computer 402, and used either on the computer or a separate computer, i.e. secondary computer after the two spectra are transmitted to it, for peak-to-peak matching, i.e. to confirm or validate that a match exists or does not exist. When both the vibrational spectrum and the mass spectrum are transmitted to the computer 402, it is apparent that the tangible medium is the computer for both spectra. For brevity, the commercial-off-the-shelf internal database can be referred to as a database and the commercial-off-the shelf computer program can be referred to as a computer program. The internal database contains includes the vibrational spectra and mass spectra of samples and analytes found in bulk solids.

It is understood that the vibrational spectrum of a solid media sample corresponds to the chemical composition based on the vibrational spectrum analysis. The same applies in that the mass spectrum of a solid media sample corresponds to the chemical composition based on the mass spectrum analysis. Thus, the vibrational spectrum and the mass spectrum of the same solid media sample is electronically compared using the peak-to-peak matching based on the internal database and computer program to determine whether the chemical composition based on the vibrational spectrum analysis matches the chemical composition based on the mass spectrum analysis. When the comparison determines that the two spectra match, the chemical composition of the solid media sample is confirmed, i.e. that a match exists. When the comparison determines that the two spectra do not match, the chemical composition of the solid media sample is not confirmed, i.e. that a match does not exist.

An alert system can then be activated on the computer 402 or user smartphone that notifies the user/operator that a match exists or does not exist. This can be based on application-specific conditions such as, for example, when at least one analyte is identified and/or confirmed, or simply when a benign substance is identified and/or confirmed. Other alert or notification methods can also be used as technology advances without detracting from the merits or generalities of the embodiments. The usefulness of the validation is quite apparent. It can be used to eliminate false positives and false negatives. It can be used as a final confirmation to determine whether further action is needed such as, for example, detaining and/or arresting individuals or contacting appropriate personnel for further action.

When additional receptacles 206 hold additional sample collection devices 100 containing solid media samples for analysis, the process above is updated by iterating the additional sample collection devices 100 through the first, second, and third positions 1104, 1106, and 1107, respectively. When the first sample collection device 100A is advanced from the first position 1104 to the second position 1106, the second sample collection device 100B advances to the first position. The process discussed above is followed. The vibrational spectrum for the solid media sample in the second sample collection device 100B is obtained. The second sample collection device 100B is then advanced to the second position 1104, where solvent is pumped into the second sample collection device. The second sample collection device 100B is then advanced to the third position 1108. High voltage is applied to the second sample collection device 100B and the resulting products from the solid media sample is sprayed into the mass spectrometer's sampling inlet 902. The mass spectrum is obtained for the solid media sample in the second sample collection device 100B and the comparison of the vibrational spectrum to the mass spectrum can occur as described above.

Iterations and analysis of remaining solid media samples in subsequent sample collection devices 100, i.e. third through eighth sample collection devices 100C through 100H in FIG. 11, can continue until there is no additional solid media samples in subsequent sample collection devices needing analysis and comparison or until the user/operator decides to end the analysis. It is understood that the user/operator can replace sample collection devices 100 that have had their solid media samples analyzed with new sample collection devices containing solid media samples that have not been analyzed. The process would then iterate and continue as described above.

While the embodiments have been described, disclosed, illustrated and shown in various terms of certain embodiments or modifications which it has presumed in practice, the scope is not intended to be, nor should it be deemed to be, limited thereby and such other modifications or embodiments as may be suggested by the teachings herein are particularly reserved especially as they fall within the breadth and scope of the claims here appended.

What is claimed is:

1. A method of identifying and confirming the chemical composition of a solid media sample, the method comprising:

(a) providing a system, comprising:

a motorized platform, a computer, a vibrational spectrometer, a syringe pump, and a mass spectrometer having a high voltage power source and a sampling inlet;

said motorized platform having a rotary disc, an electric motor, and a controller, wherein said rotary disc is electromechanically-coupled to said electric motor and said controller, wherein said rotary disc having a first side, a second side, an outer edge, and a central longitudinal axis, wherein said computer is configured to communicate with each of said controller, said vibrational spectrometer, said syringe pump, and said mass spectrometer, wherein said computer is configured to provide instructions to said controller, said instructions causing said controller to actuate said electric motor to advance said rotary disc about said central longitudinal axis;

wherein a plurality of receptacles, defined as a first through a last receptacle, extend through said rotary disc from said first side to said second side, wherein said first through last receptacles are each configured to removably-hold a corresponding first sample collection device through a last sample collection device;

(b) collecting a first solid media sample, placing said first solid media sample in said first sample collection device, and placing said first sample collection device in said first receptacle;

(c) instructing said controller to actuate said electric motor to advance said rotary disc to position said first sample collection device at a first position, said first position corresponding to the location of said vibrational spectrometer, and collecting a vibrational spectrum of said first solid media sample with said vibrational spectrometer, and outputting said vibrational spectrum to a tangible medium;

(d) instructing said controller to actuate said electric motor to advance said rotary disc to position said first sample collection device at a second position, said second position corresponding to a solvent fill position, and instructing said syringe pump to pump solvent into said first sample collection device;

(e) instructing said controller to actuate said electric motor to advance said rotary disc to position said first sample collection device at a third position, said third position corresponding to high voltage application and mass spectrum collection, wherein said high voltage power source is electrically-coupled with said first sample collection device at said third position;

(f) applying a high voltage from said high voltage power source to said first sample collection device, said high voltage application causing said solvent and resulting extracted products from said first solid media sample to be sprayed into said sampling inlet; and (g) collecting a mass spectrum of said resulting extracted products from said first solid media sample, and outputting said mass spectrum to said tangible medium.

2. The method according to claim 1, further comprising:

wherein said tangible medium is said computer;

wherein said computer having stored thereon an internal database of vibrational spectra and mass spectra of samples and analytes found in bulk solids, wherein said computer is configured to perform peak-to-peak matching of said vibrational spectrum to said mass spectrum;

said vibrational spectrum corresponding to a chemical composition based on vibrational spectrum analysis and said mass spectrum corresponding to a chemical composition based on mass spectrum analysis;

electronically comparing said vibrational spectrum of said first solid media sample to said mass spectrum of said first solid media sample using said peak-to-peak matching to determine whether said chemical composition based on vibrational spectrum analysis matches said chemical composition based on mass spectrum analysis;

wherein when said comparison determines that said vibrational spectrum and said mass spectrum match, the chemical composition of the solid media sample is confirmed;

wherein when said comparison determines that said vibrational spectrum and said mass spectrum do not match, the chemical composition of the solid media sample is not confirmed.

3. The method according to claim 2, wherein when it is determined that the chemical composition of additional solid media samples is to be determined, the method comprising:

updating to a second sample collection device through said last sample collection device, placing said second through said last sample collection devices in said second through said last receptacles; and iterating through tasks (b) through (g) with a second solid media sample through a last solid media sample until there are no additional solid media samples remaining.

4. The method according to claim 2, further comprising wherein when it is determined that said first solid media sample contains at least one analyte, determining said at least one analyte's relative concentration.

5. The method according to claim 1, wherein said plurality of receptacles are axially-spaced at equal distance about said central longitudinal axis.

6. The method according to claim 1, wherein each of said first sample collection device through said last sample collection device, comprising:

a proximal end, a distal end, and a hole at said distal end;

wherein each of said first sample collection device through said last sample collection device is hollow, configured to hold solid media samples, and are constructed of a conductive polymer, said conductive polymer including a mixture of carbon nanotubes and a polymer.

7. The method according to claim 1, wherein said vibrational spectrometer is a Raman spectrometer.

8. The method according to claim 1, wherein said vibrational spectrometer is an infrared spectrometer.

9. The method according to claim 1, wherein said vibrational spectrometer is a benchtop vibrational spectrometer or a handheld vibrational spectrometer.

10. The method according to claim 1, wherein said mass spectrometer is a portable mass spectrometer or a benchtop mass spectrometer.

11. The method according to claim 1, wherein said syringe pump is in fluid communication with said second position.

12. The method according to claim 1, wherein said syringe pump is configured to pump solvent at a flow rate of about six milliliters per minute.

13. The method according to claim 1, wherein said syringe pump is configured to pump about six milliliters of solvent.

14. The method according to claim 1, wherein said high voltage is a range of about 4 kV to about 5 kV.

15. The method according to claim 1, wherein said high voltage is about 7 kV.

16. The method according to claim 1, wherein said high voltage is a range of about 4 kV to about 7 kV.

17. The method according to claim 1, wherein said plurality of receptacles is a range of about four to about twelve receptacles.

18. The method according to claim 1, wherein said plurality of receptacles are apertures through said rotary disc.

19. The method according to claim 6, wherein said polymer is selected from the group consisting of polyethylene terephthalate, acrylonitrile butadiene styrene, polylactic acid, polyetherketoneketone, polyether ether ketone, polycarbonate, polyphenylene sulfide, polyvinylidene fluoride, and combinations thereof.

20. The method according to claim 1, wherein said rotary disc is constructed of a non-conductive, chemically inert plastic.

* * * * *